(12) United States Patent
Thornbury et al.

(10) Patent No.: US 9,877,940 B2
(45) Date of Patent: Jan. 30, 2018

(54) ANTHRAQUINONE COMPOUNDS AND THEIR USES

(71) Applicant: DUNDALK INSTITUTE OF TECHNOLOGY, Dundalk, County Louth (IE)

(72) Inventors: Keith Thornbury, Banbridge (GB); Gerard Patrick Sergeant, Belfast Antrim (GB); Noel McHale, Belfast Antrim (GB); Subhrangsu Roy, West Ben (IN); Mark Anthony Hollywood, Saintfield Down (GB)

(73) Assignee: Dundalk Institute of Technology, Dundalk, County Louth (IE)

( * ) Notice: Subject to any disclaimer, the term of this patent is extended or adjusted under 35 U.S.C. 154(b) by 0 days.

(21) Appl. No.: 14/815,135

(22) Filed: Jul. 31, 2015

(65) Prior Publication Data

US 2016/0243066 A1    Aug. 25, 2016

Related U.S. Application Data

(63) Continuation of application No. 13/824,193, filed as application No. PCT/EP2011/066053 on Sep. 15, 2011, now abandoned.

(30) Foreign Application Priority Data

Sep. 17, 2010   (EP) .................................... 10009835
Aug. 29, 2011   (GB) .................................... 1114855.8

(51) Int. Cl.
| | | |
|---|---|---|
| *A61K 31/185* | (2006.01) | |
| *A61K 31/196* | (2006.01) | |
| *A61K 31/192* | (2006.01) | |
| *A61K 31/277* | (2006.01) | |
| *C07C 309/53* | (2006.01) | |
| *C07C 229/34* | (2006.01) | |

(52) U.S. Cl.
CPC .......... *A61K 31/196* (2013.01); *A61K 31/185* (2013.01); *A61K 31/192* (2013.01); *A61K 31/277* (2013.01); *C07C 309/53* (2013.01); *C07C 229/34* (2013.01); *C07C 2601/04* (2017.05); *C07C 2601/08* (2017.05); *C07C 2601/18* (2017.05); *C07C 2602/08* (2017.05); *C07C 2602/10* (2017.05); *C07C 2603/18* (2017.05); *C07C 2603/24* (2017.05)

(58) Field of Classification Search
CPC .............. C07C 309/53; C07C 2103/24; C07C 2101/04; C07C 2101/08; C07C 2101/18; C07C 2102/08; C07C 2102/10; C07C 2103/18; C07C 2601/04; C07C 2601/08; C07C 2601/18; C07C 2602/08; C07C 2602/10; C07C 2603/18; C07C 2603/24; C07C 229/34; A61K 31/185; A61K 31/192; A61K 31/196; A61K 31/277
See application file for complete search history.

(56) References Cited

U.S. PATENT DOCUMENTS

| | | |
|---|---|---|
| 3,984,429 A | 10/1976 | Peel et al. |
| 2004/0019042 A1 | 1/2004 | Lee et al. |
| 2005/0272767 A1 | 12/2005 | Yoshihiro et al. |

FOREIGN PATENT DOCUMENTS

| | | | |
|---|---|---|---|
| DE | 456114 | 2/1928 | |
| EP | 1634595 A1 | 3/2006 | |
| JP | 2008214211 A | 9/2008 | |
| WO | WO 2008107211 A2 * | 9/2008 | ........... C07C 229/74 |

OTHER PUBLICATIONS

Hubner et. al., Human Molecular Genetics, 2002, Oxford University Press, vol. 11(20), pp. 2435-2445.*
Alvina et. al., The Journal of Neuroscience, 2010, Society for Neuroscience, vol. 30(21), pp. 7249-7257.*
International Search Report dated Feb. 13, 2012 for PCT International Application No. PCT/EP2011/066053.
Weyler et al., "Combinatorial Synthesis of Anilinoanthraquinone Derivatives and Evaluation as Non-Nucleotide-Derived P2Y2 Receptor Antagonists," Bioorganic & Medicinal Chemistry Letters, 2007, vol. 18, No. 1, pp. 223-227.
Baqi, Y. et al., "High-Affinity, Non-Nucleotide-Derived Competitive Antagonists of Platelet P2Y12 Receptors," J. Med. Chem., 2009, vol. 52, No. 12, pp. 3784-3793.
Baqi, Y. et al., Structure-Activity Relationships of Anthraquinone Derivatives Derived from Bromaminic Acid as Inhibitors of Ectonucleoside Triphosphate Diphosphohydrolases (E-NTPDases), Purinergic Signalling, 2009, vol. 5, No. 1, pp. 91-106.
Baqi, Y. et al., "Development of Potent and Selective Inhibitors of ecto-5'-Nucleotidase Based on an Anthraquinone Scaffold," 2010, J. Med. Chem., vol. 53, No. 5, pp. 2076-2086.
Baqi, Y. et al., "Discovery of Potent Competitive Antagonists and Positive Modulators of the P2X2 Receptor," J. Med. Chem., 2011, vol. 54, No. 3, pp. 817-830.

(Continued)

*Primary Examiner* — Sarah Pihonak
(74) *Attorney, Agent, or Firm* — Saul Ewing Arnstein & Lehr LLP; Kathryn Doyle; Domingos J. Silva

(57) ABSTRACT

The present invention relates to a compound comprising a substituted or unsubstituted anthraquinone, or a salt or isomer thereof, for use in treating a disorder caused by or associated with dysfunctional ion channel activity. The invention finds utility in the treatment of disorders associated with smooth muscle tone and contraction, such as but not limited to partial hypertension; myocardial infarction; faecal incontinence; constipation; gastro oesophageal reflux; impaired gastrointestinal passage; urinary incontinence; erectile dysfunction; and asthma.

7 Claims, 7 Drawing Sheets

(56) References Cited

OTHER PUBLICATIONS

Gao, S. et al., "Bioactivities of Simplified Adociaquinone B and Naphthoquinone Derivatives Against Cdc25B, MKP-1, and MKP-3 Phosphatases," 2009, Bioorganic & Medicinal Chemistry, vol. 17, No. 6, pp. 2276-2281.
Hede, S.E. et al., "P2Y2 and P2Y4 Receptors Regulate Pancreatic Ca2+-activated K+ Channels Differently," Eur. J. Physiol., 2005, vol. 450, No. 6, pp. 429-436.
Tuluc, F. et al., "P2-Receptor Antagonists: IV. Blockage of P2-receptor Subtyptes and ecto-Nucleotidases by compounds Related to Reactive Blue 2," Naunyn-Schmiedeberg's Arch. Pharmacol., 1998, vol. 357, No. 2, pp. 111-120.
XP-002662943, STN Database Accession No. 1964:462083, Tokumitsu, T. et al., "Paper Chromatography of Anthraquinone Acid Dyes," Kogyo Kagaku Zasshi, 1964, vol. 67, No. 1, pp. 197-200. (Abstract Only).
XP-002662942, STN Accession No. 1979:205642, Fisichella, S. et al., "Thermodynamics of Dyeing of Anthraquinonoid Dyes for Viscose Rayon," 1978, Annali di Chimica, vol. 68(5-6), pp. 503-506.
Patidar, A.K. et al., "Bioisosteres and Bioisosteric Replacement: A Useful Strategy for Structural Modification of Lead Compound in Drug Design and in Drug Discovery," International Journal of Pharmaceutical Research and Development, 2010, vol. 2, No. 3, pp. 1-12.

* cited by examiner 100 nm $Ca^{2+}$

1 μm $Ca^{2+}$

1 μm $Ca^{2+}$

Effect of SR-5-6 on STOC activity
Holding at -30 mV

Control

SR-5-6 (10 µM)

Concentration dependent effect of SR-5-6

Summary Data

ANTHRAQUINONE COMPOUNDS AND THEIR USES

CROSS-REFERENCE TO RELATED APPLICATIONS

This application is a continuation of, and claims priority to, U.S. application Ser. No. 13/824,193, filed Jul. 17, 2013, which is the U.S. national phase application filed under 35 U.S.C. § 371 claiming priority to International Patent Application No. PCT/EP2011/066053, filed Sep. 15, 2011, which claims priority to European Application No. 10 009 835.9, filed Sep. 17, 2010 and Great Britain Application No. 1 114 855.8, filed Aug. 29, 2011, all of which applications are hereby incorporated herein by reference in their entireties.

BACKGROUND TO THE INVENTION

Smooth muscle has been implicated to play a role in a large number of diseases affecting the urinary tract (e.g. urinary incontinence), the digestive system (e.g. irritable bowel syndrome), the circulatory system and the reproductive system. Large conductance potassium ion channels (BK channels), also called Maxi-K or slo1, are membrane associated ion channels, which conduct potassium ions across a cell membrane. BK channels are present in a wide variety of tissues throughout the body, and are activated (opened) or deactivated (closed) by two physiologically relevant factors; a change in intracellular calcium ion ($Ca^{2+}$) concentration, or a change in the electrical potential across the cell membrane. An increase in the activity of BK channels leads to a decrease in cell excitability and a concurrent hyperpolarization of the cell membrane. As such, BK channels are critical in the regulation of smooth muscle tone, neuronal excitability, secretion, contractility to name a few.

Drugs that activate or open BK channels are in high demand for their potential clinical use. Primary indications for BK channel openers include urinary incontinence, irritable bowel syndrome, diabetes and arterial hypertension, cardiovascular diseases including myocardial infarction, erectile dysfunction, airway constriction and preterm labour caused by overactive uterine contractions.

Only one BK opener, Andolast (CR 2039, N-4-(5-tetrazolyl)-phenyl-4-(5-tetrazolyl)-benzamide) is currently in development, in phase 3 clinical trials in bronchial pneumonia patients in a comparison study with inhaled corticosteroids. Three other BK openers have failed in clinical development and have been discontinued. This class of drugs is however of exceptional importance and commercial value and has been of interest as a target for drug discovery, because experimental evidence suggests BK Channels play a pivotal and specific role in many pathophysiological conditions. This class of drug will elicit smooth muscle relaxation. As a result, in diseases such as urinary incontinence, where a hallmark of the disease or condition is overactive spastic smooth muscle, a BK channel opener will relax the spastic muscle, returning it to normal functioning and decreasing the urge that accompanies urinary incontinence.

The current market leader for the treatment of urinary incontinence is Detrol® (marketed by Pfizer), and all other drugs on the market used to treat this condition are of the same classification; muscarinic antagonists. Detrol® and similar muscarinic antagonists bind to, but do not activate muscarinic cholinergic receptors. Rather they act by blocking the action of endogenous acetylcholine, a neurotransmitter found in both peripheral and central nervous systems. These agents have widespread effects including actions on the iris and ciliary muscles in the eye and on organs such as the heart and vasculature, secretions associated with the respiratory tract, the GI system, salivary glands, and the CNS—contributing to a plethora of side effects from the drugs. The most common side effects from muscarinic antagonists like Detrol® include blurred vision, constipation, dizziness, drowsiness, dry eyes, dry mouth, headache, indigestion, stomach pain. More severe side effects can include severe allergic reactions such as a rash, hives, itching, difficulty breathing, tightness in the chest, swelling of the mouth, face, lips, or tongue, unusual hoarseness, chest pain, confusion, difficult or painful urination, disorientation, fast or irregular heart beat, hallucinations, memory problems, severe dizziness, swelling of the hands, ankles or feet.

Approximately one in 6 people in the USA are affected by overactive bladder. The condition is the result of bladder muscle contraction and squeezing too often, causing frequent and strong urges to urinate, in addition to undesired wetting incidences affecting sleep, social life, health and well-being, relationships and feelings of self-worth.

SUMMARY OF THE INVENTION

According to a first aspect of the present invention, there is provided a compound comprising a substituted or unsubstituted anthraquinone, or a salt or isomer thereof, for use in treating a disorder caused by or associated with dysfunctional ion channel activity.

Optionally, the compound has the general formula (I):

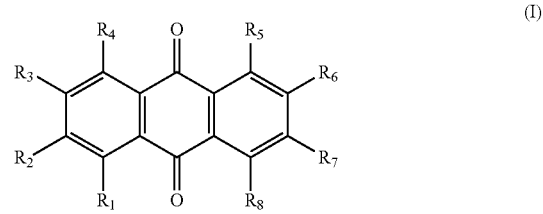

(I)

wherein;

$R_1$-$R_4$ and $R_7$ are each a hydrogen atom;

$R_5$ and $R_8$, which can be the same or different, are each independently selected from a hydrogen atom; and an amine, optionally a secondary amine; and $R_6$ is independently selected from a hydrogen atom or an alkyl group; further optionally a sulfonate or a carboxyl group.

Optionally, $R_6$ is independently selected from a hydrogen atom or an alkyl group; further optionally a sulfonate, carboxyl, or a tetrazole group.

According to a second aspect of the present invention there is provided a compound having the general formula (I):

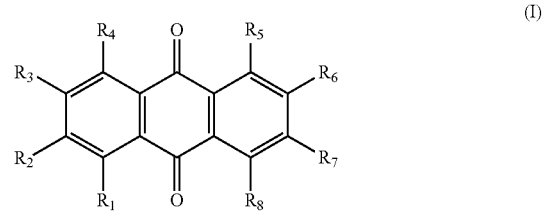

(I)

wherein;

$R_1$-$R_4$ and $R_7$ are each a hydrogen atom;

$R_5$ and $R_8$, which can be the same or different, are each independently selected from a hydrogen atom; and an amine, optionally a secondary amine; and $R_6$ is independently selected from a hydrogen atom or a alkyl group; further optionally a sulfonate or a carboxyl group.

Optionally, $R_6$ is independently selected from a hydrogen atom or an alkyl group; further optionally a sulfonate, carboxyl, or a tetrazole group.

Optionally, the compound comprises a substituted anthraquinone, or a salt or isomer thereof.

Optionally, the compound comprises an acid dye, or a salt or isomer thereof, which can be substituted or unsubstituted. Further optionally, the acid dye, or a salt or isomer thereof, is substituted.

Optionally, the compound comprises an acid dye selected from an acid blue dye and an acid green dye, or a salt or isomer each thereof, which can be substituted or unsubstituted.

Optionally, the compound comprises a substituted anthraquinone and has the general formula (IA):

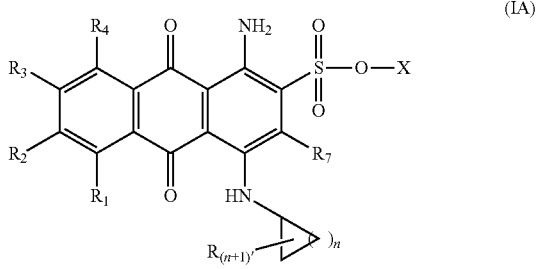

(IA)

wherein;

n is an integer from 1 to 5;

$R_1$-$R_4$ and $R_7$ are each a hydrogen atom;

X is an alkali metal cation, optionally sodium;

each $R_{(n+1)'}$ is independently selected from at least one of:
  i. a hydrogen atom;
  ii. a heteroatom selected from a halide, optionally fluoride or chloride; an oxygen atom; or an amine, optionally a primary amine;
  iii. a short chain alkyl, alkenyl, or alkynyl group, which can be branched or unbranched, substituted or unsubstituted, linear or cyclic; optionally a short chain alkyl; further optionally an ethyl, propyl, or a butyl group;
  iv. a short chain aza-alkyl, aza-alkenyl, or aza-alkynyl group, which can be branched or unbranched, substituted or unsubstituted, linear or cyclic;
  v. a short chain alkoxyl, alkenoxyl, or alkynoxyl group, which can be branched or unbranched, substituted or unsubstituted, linear or cyclic;
  vi. a short chain thio-alkyl, thio-alkenyl, or thio-alkynyl group, which can be branched or unbranched, substituted or unsubstituted, linear or cyclic;
  vii. a short chain halo-alkyl, halo-alkenyl, or halo-alkynyl group, which can be branched or unbranched, substituted or unsubstituted, linear or cyclic; optionally a fluorinated methyl group; further optionally a trifluoromethyl group;
  viii. a nitrile, hydroxyl or ester group;
  ix. a sulfonate or carboxyl group; and
  x. a tetrazole;

or a pharmaceutically acceptable salt, hydrate, or isomer thereof.

By the term "linear" is meant a molecule comprising at least two atoms, any of which can be the same or different, wherein each atom of the molecule is bonded to an adjacent atom in a substantially straight series. Each atom can be bonded to an adjacent carbon atom by a single-, double-, triple-, or higher order-bond.

By the term "cyclic" is meant a molecule comprising at least three atoms, any of which can be the same or different, wherein each atom of the molecule is bonded to an adjacent atom in a substantially continuous series having no terminal atoms. Each atom can be bonded to an adjacent carbon atom by a single-, double-, triple-, or higher order-bond.

By the term "branched" is meant a molecule comprising at least three atoms, any of which can be the same or different, bonded in a substantially straight series, wherein the molecule further comprises at least one other atom, which is not bonded to either of the terminal atoms of the substantially straight series. Each atom can be bonded to an adjacent atom by a single-, double-, triple-, or higher order-bond.

By "short chain" is meant a polyatomic molecule comprising at least one carbon atom. Optionally, the polyatomic molecule comprises 1-6 carbon atoms. Further optionally, the polyatomic molecule comprises 1-3 carbon atoms. Optionally, the alkyl group comprises two carbon atoms. Optionally, the alkyl group is an ethyl group.

Alternatively, the alkyl group comprises three carbon atoms. Optionally, the alkyl group is a propyl group, optionally an isopropyl group.

Further alternatively, the alkyl group comprises four carbon atoms. Optionally, the alkyl group is a butyl group, optionally a tertiary butyl group.

Optionally, the alkenyl group comprises at least six carbon atoms. Further optionally, the alkenyl group is a cyclic, for example a phenyl, group.

Optionally, the short chain alkyl, alkenyl, or alkynyl group is a polycyclic group.

Optionally, the polycyclic group is a cycloalkane, cycloalkene, or cycloalkyne. Still further optionally, the polycyclic group comprises a cycloalkene, for example a phenyl, group; and a cycloalkane fused, optionally ortho-fused, thereto. Optionally or additionally, the polycyclic group comprises a cycloalkene, for example a phenyl, group; and a cycloalkane fused, optionally ortho-fused, thereto, wherein the cycloalkane comprises 1 to 9 carbon atoms; optionally 3 to 6 carbon atoms.

Optionally or additionally, the polycyclic group comprises a cycloalkene, for example a phenyl, group; and a cycloalkane fused, optionally ortho-fused, thereto, wherein the cycloalkane comprises cyclopentane.

Optionally or additionally, the polycyclic group comprises a cycloalkene, for example a phenyl, group; and a cycloalkane fused, optionally ortho-fused, thereto, wherein the cycloalkane comprises cyclohexane.

Optionally, the polycyclic group comprises a cycloalkene, for example a phenyl, group; and a cycloalkene fused, optionally ortho-fused, thereto. Optionally or additionally, the polycyclic group comprises a cycloalkene, for example a phenyl group; and a cycloalkene fused, optionally ortho-fused, thereto, wherein each cycloalkene comprises 1 to 9 carbon atoms.

Optionally, the polycyclic group comprises naphthalene.

Optionally, the polycyclic group comprises indene.

Optionally, the polycyclic group comprises tetralin (1,2, 3,4-tetrahydronaphthalene).

Optionally, the polycyclic group comprises fluorene, optionally 9H-fluorene.

Optionally, the halo-alkyl group comprises at least one carbon atom and at least one fluorine atom. Optionally, the haloalkyl group is a trifluoromethyl group. Optionally, the haloalkyl group comprises a trifluoromethyl group bonded to at least one heteroatom. Further optionally, the haloalkyl group comprises a trifluoromethyl group bonded to at least one oxygen atom (—O—CF$_3$).

Optionally, the alkoxyl group comprises at least one carbon atom and at least one oxygen atom. Optionally, the alkoxyl group is a methoxyl group.

Optionally, the alkenoxyl group is a carboxyl group.

Optionally, n is selected from 1, 2, 3, 4, and 5.

Optionally, n is 1. Further optionally or additionally, each $R_{(n+1)'}$ is a hydrogen atom. Further optionally, the compound is sodium 1-amino-4-(cyclopropylamino)-9,10-dioxo-9,10-dihydroanthracene-2-sulfonate.

Optionally, n is 2. Further optionally or additionally, each $R_{(n+1)'}$ is a hydrogen atom. Further optionally, the compound is sodium 1-amino-4-(cyclobutylamino)-9,10-dioxo-9,10-dihydroanthracene-2-sulfonate.

Optionally, n is 3. Further optionally or additionally, each $R_{(n+1)'}$ is a hydrogen atom. Further optionally, the compound is sodium 1-amino-4-(cyclopentylamino)-9,10-dioxo-9,10-dihydroanthracene-2-sulfonate.

Optionally, n is 4. Further optionally or additionally, each $R_{(n+1)'}$ is a hydrogen atom. Further optionally, the compound is sodium 1-amino-4-(cyclohexylamino)-9,10-dioxo-9,10-dihydroanthracene-2-sulfonate.

Optionally, n is 4, and forms a cyclohexane. Further optionally or additionally, at least one $R_{(n+1)'}$ is a trifluoromethyl group. Still further optionally, $R_{(n+1)'}$ is a trifluoromethyl group attached at the β-position of the cyclohexane. Further optionally, the compound is sodium 1-amino-9,10-dioxo-4-(3-(trifluoromethyl)cyclohexylamino)-9,10-dihydroanthracene-2-sulfonate.

Optionally, n is 4, and forms a cyclohexane. Further optionally or additionally, at least one $R_{(n+1)'}$ is an alkyl, optionally a butyl, group. Still further optionally, at least one $R_{(n+1)'}$ is a alkyl, optionally a tertiary butyl group; optionally attached at the 4-position of the cyclohexane. Further optionally, the compound is sodium 1-amino-4-(4-tert-butylcyclohexylamino)-9,10-dioxo-9,10-dihydroanthracene-2-sulfonate.

Optionally, n is 5. Further optionally or additionally, each $R_{(n+1)'}$ is a hydrogen atom. Further optionally, the compound is sodium 1-amino-4-(cycloheptylamino)-9,10-dioxo-9,10-dihydroanthracene-2-sulfonate.

Optionally, n is 4. Further optionally, the compound has the general formula (IB):

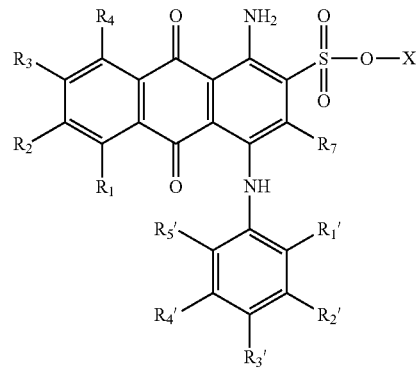

(IB)

Optionally, $R_{1'}$ and $R_{5'}$, which can be the same or different, are each independently selected from at least one of each of:
  i. a hydrogen atom;
  ii. a heteroatom selected from a halide, optionally fluoride or chloride; or an oxygen atom;
  iii. a short chain alkyl, alkenyl, or alkynyl group, which can be branched or unbranched, substituted or unsubstituted, linear or cyclic; optionally a short chain alkyl; further optionally an ethyl group;
  iv. a short chain alkoxyl, alkenoxyl, or alkynoxyl group, which can be branched or unbranched, substituted or unsubstituted, linear or cyclic; and
  v. a short chain halo-alkyl, halo-alkenyl, or halo-alkynyl group, which can be branched or unbranched, substituted or unsubstituted, linear or cyclic.

Further optionally, $R_{1'}$ and $R_{5'}$, which can be the same or different, are each independently selected from at least one of each of:
  i. a hydrogen atom;
  ii. fluoride;
  iii. a polycyclic group selected from a cycloalkane, cycloalkene, or cycloalkyne;
  iv. a methoxyl group; and
  v. a trifluoromethyl group.

Optionally, $R_{2'}$ and $R_{4'}$, which can be the same or different, are each independently selected from at least one of each of:
  i. a hydrogen atom;
  ii. a heteroatom selected from a halide, optionally fluoride or chloride; an oxygen atom; or an amine, optionally a primary amine;
  iii. a short chain halo-alkyl, halo-alkenyl, or halo-alkynyl group, which can be branched or unbranched, substituted or unsubstituted, linear or cyclic;
  iv. a sulfonate or carboxyl group;
  v. a short chain alkyl, alkenyl, or alkynyl group, which can be branched or unbranched, substituted or unsubstituted, linear or cyclic;
  vi. a short chain alkoxyl, alkenoxyl, or alkynoxyl group, which can be branched or unbranched, substituted or unsubstituted, linear or cyclic;
  vii. a nitrile group;
  viii. a tetrazole; and
  ix. a hydroxyl group.

Further optionally, $R_{2'}$ and $R_{4'}$, which can be the same or different, are each independently selected from at least one of each of:

i. a hydrogen atom;
ii. fluoride;
iii. chloride;
iv. a trifluoromethyl group;
v. a trifluoromethyl group bonded to at least one oxygen atom (—O—CF$_3$);
vi. a methyl group;
vii. an ethyl group;
viii. an isopropyl group;
ix. a tert-butyl group;
x. a cyclopropyl group;
xi. a nitrile group;
xii. a methoxyl group;
xiii. a ethoxyl group;
xiv. an isopropoxyl group;
xv. an amine, optionally a primary amine;
xvi. a polycyclic group selected from a cycloalkane, cycloalkene, or cycloalkyne;
xvii. a benzyl group;
x. a tetrazole; and
xviii. a hydroxyl group.

Optionally, $R_{3'}$ is independently selected from at least one of each of:
i. a hydrogen atom;
ii. a short chain halo-alkyl, halo-alkenyl, or halo-alkynyl group, which can be branched or unbranched, substituted or unsubstituted, linear or cyclic;
iii. a heteroatom selected from a halide, optionally fluoride or chloride; an oxygen atom; or an amine, optionally a primary amine;
iv. a short chain alkyl, alkenyl, or alkynyl group, which can be branched or unbranched, substituted or unsubstituted, linear or cyclic
v. a short chain alkoxyl, alkenoxyl, or alkynoxyl group, which can be branched or unbranched, substituted or unsubstituted, linear or cyclic; and
vi. a nitrile.

Further optionally, $R_{3'}$ is independently selected from at least one of each of:
i. a hydrogen atom;
ii. a trifluoromethyl group;
iii. fluoride;
iv. chloride;
v. a benzyl group;
vi. a methyl group;
vii. a methoxyl group;
viii. an amine, optionally a primary amine; and
ix. a nitrile.

Optionally, each of $R_1$-$R_5$ is a hydrogen atom. Further optionally, the compound is sodium 1-amino-9,10-dioxo-4-(phenylamino)-9,10-dihydroanthracene-2-sulfonate.

Optionally, $R_{2'}$ is a trifluoromethyl group. Further optionally or additionally, each of $R_{1'}$, and $R_3$-$R_5$ is a hydrogen atom. Further optionally, the compound is sodium 1-amino-9,10-dioxo-4-(3-(trifluoromethyl)phenylamino)-9,10-dihydroanthracene-2-sulfonate.

Optionally, $R_{1'}$ is a fluorine atom. Further optionally or additionally, $R_{5'}$ is a fluorine atom. Further optionally or additionally, each of $R_2$-$R_{4'}$ is a hydrogen atom. Further optionally, the compound is sodium 1-amino-4-(2,6-difluorophenylamino)-9,10-dioxo-9,10-dihydroanthracene-2-sulfonate.

Optionally, $R_{1'}$ is a methoxyl group. Further optionally or additionally, each of $R_{2'}$-$R_{4'}$ is a hydrogen atom. Further optionally, the compound is sodium 1-amino-4-(2-methoxyphenylamino)-9,10-dioxo-9,10-dihydroanthracene-2-sulfonate.

Optionally, $R_{2'}$ is a trifluoromethyl group. Further optionally or additionally, $R_{4'}$ is a trifluoromethyl group. Further optionally or additionally, each of $R_{1'}$, $R_{3'}$, and $R_{5'}$ is a hydrogen atom. Further optionally, the compound is sodium 4-(3,5-bis(trifluoromethyl)phenylamino)-1-amino-9,10-dioxo-9,10-dihydroanthracene-2-sulfonate.

Optionally, $R_{2'}$ is fluoride. Further optionally or additionally, $R_{4'}$ is fluoride. Further optionally or additionally, each of $R_{1'}$, $R_{3'}$, and $R_{5'}$ is a hydrogen atom. Further optionally, the compound is sodium 1-amino-4-(3,5-difluorophenylamino)-9,10-dioxo-9,10-dihydroanthracene-2-sulfonate.

Optionally, $R_{2'}$ is fluoride. Further optionally or additionally, each of $R_{1'}$ and $R_3$-$R_5$ is a hydrogen atom. Further optionally, the compound is sodium 1-amino-4-(3-fluorophenylamino)-9,10-dioxo-9,10-dihydroanthracene-2-sulfonate.

Optionally, $R_{2'}$ is a sulfonic acid group. Further optionally or additionally, each of $R_{1'}$ and $R_3$-$R_5$ is a hydrogen atom. Further optionally, the compound is sodium 1-amino-9,10-dioxo-4-(3-sulfophenylamino)-9,10-dihydroanthracene-2-sulfonate.

Optionally, $R_{2'}$ is a trifluoromethyl group. Further optionally or additionally, $R_{4'}$ is fluoride. Further optionally or additionally, each of $R_{1'}$, $R_{3'}$, and $R_{5'}$ is a hydrogen atom. Further optionally, the compound is sodium 1-amino-4-(3-fluoro-5-(trifluoromethyl)phenylamino)-9,10-dioxo-9,10-dihydroanthracene-2-sulfonate.

Optionally, $R_{2'}$ is a methyl group. Further optionally or additionally, each of $R_{1'}$ and $R_3$-$R_5$ is a hydrogen atom. Further optionally, the compound is sodium 4-(m-toluidino)-1-amino-9,10-dioxo-9,10-dihydroanthracene-2-sulfonate.

Optionally, $R_{2'}$ is a trifluoromethyl group. Further optionally or additionally, $R_{3'}$ is fluoride. Further optionally or additionally, each of $R_{1'}$, $R_{4'}$, and $R_{5'}$ is a hydrogen atom. Further optionally, the compound is sodium 1-amino-4-(4-fluoro-3-(trifluoromethyl)phenylamino)-9,10-dioxo-9,10-dihydroanthracene-2-sulfonate.

Optionally, $R_{2'}$ is an ethyl group. Further optionally or additionally, each of $R_{1'}$ and $R_3$-$R_5$ is a hydrogen atom. Further optionally, the compound is sodium 1-amino-4-(3-ethylphenylamino)-9,10-dioxo-9,10-dihydroanthracene-2-sulfonate.

Optionally, $R_{2'}$ is a trifluoromethoxyl group (—OCF$_3$). Further optionally or additionally, each of $R_{1'}$ and $R_3$-$R_5$ is a hydrogen atom. Further optionally, the compound is sodium 1-amino-9,10-dioxo-4-(3-(trifluoromethoxy)phenylamino)-9,10-dihydroanthracene-2-sulfonate.

Optionally, $R_{3'}$ is a benzyl group. Further optionally or additionally, each of $R_{1'}$, $R_{2'}$, $R_{4'}$, and $R_{5'}$ is a hydrogen atom. Further optionally, the compound is sodium 1-amino-4-(4-benzylphenylamino)-9,10-dioxo-9,10-dihydroanthracene-2-sulfonate.

Optionally, $R_{2'}$ is a trifluoromethyl group. Further optionally or additionally, $R_{3'}$ is chloride. Further optionally or additionally, each of $R_{1'}$, $R_{4'}$, and $R_{5'}$ is a hydrogen atom. Further optionally, the compound is sodium 1-amino-4-(4-chloro-3-(trifluoromethyl)phenylamino)-9,10-dioxo-9,10-dihydroanthracene-2-sulfonate.

Optionally, $R_{2'}$ is trifluoromethyl group. Further optionally or additionally, $R_{3'}$ is a methyl group. Further optionally or additionally, each of $R_{1'}$, $R_{4'}$, and $R_{5'}$ is a hydrogen atom. Further optionally, the compound is sodium 1-amino-4-(4-methyl-3-(trifluoromethyl)phenylamino)-9,10-dioxo-9,10-dihydroanthracene-2-sulfonate.

Optionally, $R_{2'}$ is chloride. Further optionally or additionally, each of $R_{1'}$, and $R_3$-$R_5$ is a hydrogen atom. Further optionally, the compound is sodium 1-amino-4-(3-chlorophenylamino)-9,10-dioxo-9,10-dihydroanthracene-2-sulfonate.

Optionally, $R_{2'}$ is a nitrile group. Further optionally or additionally, each of $R_{1'}$, and $R_{3'}$-$R_{5'}$ is a hydrogen atom. Further optionally, the compound is sodium 1-amino-4-(3-cyanophenylamino)-9,10-dioxo-9,10-dihydroanthracene-2-sulfonate.

Optionally, $R_{2'}$ is a trifluoromethyl group. Further optionally or additionally, $R_{3'}$ is a nitrile group. Further optionally or additionally, each of $R_{1'}$, $R_{4'}$, and $R_{5'}$ is a hydrogen atom. Further optionally, the compound is sodium 1-amino-4-(4-cyano-3-(trifluoromethyl)phenylamino)-9,10-dioxo-9,10-dihydroanthracene-2-sulfonate.

Optionally, $R_{2'}$ is a trifluoromethyl group. Further optionally or additionally, $R_{3'}$ is a methoxyl group. Further optionally or additionally, each of $R_{1'}$, $R_{4'}$, and $R_{5'}$ is a hydrogen atom. Further optionally, the compound is sodium 1-amino-4-(4-methoxy-3-(trifluoromethyl)phenylamino)-9,10-dioxo-9,10-dihydroanthracene-2-sulfonate.

Optionally, $R_{2'}$ is a methoxyl group. Further optionally or additionally, $R_{4'}$ is a trifluoromethyl group. Further optionally or additionally, each of $R_{1'}$, $R_{3'}$, and $R_{5'}$ is a hydrogen atom. Further optionally, the compound is sodium 1-amino-4-(3-methoxy-5-(trifluoromethyl)phenylamino)-9,10-dioxo-9,10-dihydroanthracene-2-sulfonate.

Optionally, $R_{2'}$ is a trifluoromethyl group. Further optionally or additionally, $R_{3'}$ is an amine, optionally a primary amine. Further optionally or additionally, each of $R_{1'}$, $R_{4'}$, and $R_{5'}$ is a hydrogen atom. Further optionally, the compound is sodium 1-amino-4-(4-amino-3-(trifluoromethyl)phenylamino)-9,10-dioxo-9,10-dihydroanthracene-2-sulfonate.

Optionally, $R_{2'}$ is an amine, further optionally a primary amine. Optionally or additionally, $R_{4'}$ is a trifluoromethyl group. Further optionally or additionally, each of $R_{1'}$, $R_{3'}$, and $R_{5'}$ is a hydrogen atom. Further optionally, the compound is sodium 1-amino-4-(3-amino-5-(trifluoromethyl)phenylamino)-9,10-dioxo-9,10-dihydroanthracene-2-sulfonate.

Optionally, a cycloalkane is fused, optionally ortho-fused, at $R_{4'}$ and $R_{5'}$, wherein the cycloalkane comprises cyclohexane. Further optionally or additionally, each of $R_{1'}$-$R_{3'}$ is a hydrogen atom. Further optionally, the compound is sodium 1-amino-9,10-dioxo-4-(5,6,7,8-tetrahydronaphthalen-1-ylamino)-9,10-dihydroanthracene-2-sulfonate.

Optionally, a cycloalkane is fused, optionally ortho-fused, at $R_{2'}$ and $R_{3'}$, wherein the cycloalkane comprises cyclopentane. Further optionally or additionally, each of $R_{1'}$, $R_{4'}$, $R_{5'}$ is a hydrogen atom. Further optionally, the compound is sodium 1-amino-4-(2,3-dihydro-1H-inden-5-ylamino)-9,10-dioxo-9,10-dihydroanthracene-2-sulfonate.

Optionally, a cycloalkene is fused, optionally ortho-fused, at $R_{4'}$ and $R_{5'}$, wherein the cycloalkene comprises benzene. Further optionally or additionally, each of $R_{1'}$-$R_{3'}$ is a hydrogen atom. Further optionally, the compound is sodium 1-amino-4-(naphthalen-1-ylamino)-9,10-dioxo-9,10-dihydroanthracene-2-sulfonate.

Optionally, $R_{2'}$ is a benzyl group. Further optionally or additionally, each of $R_{1'}$ and $R_{3'}$-$R_{5'}$ is a hydrogen atom. Further optionally, the compound is sodium 1-amino-4-(3-benzylphenylamino)-9,10-dioxo-9,10-dihydroanthracene-2-sulfonate.

Optionally, a cycloalkene is fused, optionally ortho-fused, at $R_{2'}$ and $R_{3'}$, wherein the cycloalkene comprises benzene. Further optionally or additionally, each of $R_{1'}$, $R_{4'}$, $R_{5'}$ is a hydrogen atom. Further optionally, the compound is sodium 1-amino-4-(naphthalen-2-ylamino)-9,10-dioxo-9,10-dihydroanthracene-2-sulfonate.

Optionally, a cycloalkane is fused, optionally ortho-fused, at $R_{2'}$ and $R_{3'}$, wherein the cycloalkane comprises cyclohexane. Further optionally or additionally, each of $R_{1'}$, $R_{4'}$, $R_{5'}$ is a hydrogen atom. Further optionally, the compound is sodium 1-amino-9,10-dioxo-4-(5,6,7,8-tetrahydronaphthalen-2-ylamino)-9,10-dihydroanthracene-2-sulfonate.

Optionally, $R_{2'}$ is a cyclopropyl group. Further optionally or additionally, each of $R_{1'}$ and $R_{3'}$-$R_{5'}$ is a hydrogen atom. Further optionally, the compound is sodium 1-amino-4-(3-cyclopropylphenylamino)-9,10-dioxo-9,10-dihydroanthracene-2-sulfonate.

Optionally, $R_{2'}$ is an isopropyl group. Further optionally or additionally, each of $R_{1'}$ and $R_{3'}$-$R_{5'}$ is a hydrogen atom. Further optionally, the compound is sodium 1-amino-4-(3-isopropylphenylamino)-9,10-dioxo-9,10-dihydroanthracene-2-sulfonate.

Optionally, $R_{2'}$ is a tert-butyl group. Further optionally or additionally, each of $R_{1'}$ and $R_{3'}$-$R_{5'}$ is a hydrogen atom. Further optionally, the compound is sodium 1-amino-4-(3-tert-butylphenylamino)-9,10-dioxo-9,10-dihydroanthracene-2-sulfonate.

Optionally, $R_{2'}$ is an ethoxyl group. Further optionally or additionally, each of $R_{1'}$ and $R_{3'}$-$R_{5'}$ is a hydrogen atom. Further optionally, the compound is sodium 1-amino-4-(3-ethoxyphenylamino)-9,10-dioxo-9,10-dihydroanthracene-2-sulfonate.

Optionally, $R_{2'}$ is an isopropoxyl group. Further optionally or additionally, each of $R_{1'}$ and $R_{3'}$-$R_{5'}$ is a hydrogen atom. Further optionally, the compound is sodium 1-amino-4-(3-isopropoxyphenylamino)-9,10-dioxo-9,10-dihydroanthracene-2-sulfonate.

Optionally, $R_{1'}$ is a methoxyl group. Further optionally or additionally, $R_{4'}$ is a trifluoromethyl group. Further optionally or additionally, each of $R_{2'}$, $R_{3'}$, and $R_{5'}$ is a hydrogen atom. Further optionally, the compound is sodium 1-amino-4-(2-methoxy-5-(trifluoromethyl)phenylamino)-9,10-dioxo-9,10-dihydroanthracene-2-sulfonate.

Optionally, $R_{2'}$ is a hydroxyl group. Further optionally or additionally, each of $R_{1'}$ and $R_{3'}$-$R_{5'}$ is a hydrogen atom. Further optionally, the compound is sodium 1-amino-4-((3-hydroxyphenyl)amino)-9,10-dioxo-9,10-dihydroanthracene-2-sulfonate.

Optionally, a cycloalkene is fused, optionally ortho-fused, at $R_{2'}$ and $R_{3'}$, wherein the cycloalkene comprises cyclopentane. Further optionally or additionally, the cycloalkene comprises indene. Further optionally, indene is fused, optionally ortho-fused, at $R_{2'}$ and $R_{3'}$. Further optionally, the cyclopentane ring of indene is fused, optionally ortho-fused, at $R_{2'}$ and $R_{3'}$. Further optionally or additionally, each of $R_{1'}$, $R_{4'}$, $R_{5'}$ is a hydrogen atom. Further optionally, the compound is sodium 4-((9H-fluoren-2-yl)amino)-1-amino-9,10-dioxo-9,10-dihydroanthracene-2-sulfonate.

Optionally, $R_{2'}$ is a polycyclic group selected from a cycloalkane, cycloalkene, or cycloalkyne. Further optionally, $R_{2'}$ is a phenyl group. Further optionally or additionally, each of $R_{1'}$, and $R_{3'}$-$R_{5'}$ is a hydrogen atom. Further optionally, the compound is sodium 4-([1,1'-biphenyl]-3-ylamino)-1-amino-9,10-dioxo-9,10-dihydroanthracene-2-sulfonate.

Optionally, $R_{1'}$ is an ethyl group. Further optionally or additionally, each of $R_{2'}$-$R_{5'}$ is a hydrogen atom. Further optionally, the compound is sodium 1-amino-4-((2-ethylphenyl)amino)-9,10-dioxo-9,10-dihydroanthracene-2-sulfonate.

Optionally, $R_{3'}$ is an ethyl group. Further optionally or additionally, each of $R_{1'}$, $R_{2'}$, $R_{4'}$, and $R_{5'}$ is a hydrogen atom. Further optionally, the compound is sodium 1-amino-4-((4-ethylphenyl)amino)-9,10-dioxo-9,10-dihydroanthracene-2-sulfonate.

Optionally, $R_{5'}$ is an isopropyl group. Further optionally or additionally, each of $R_{1'}$-$R_{4'}$ is a hydrogen atom. Further optionally, the compound is sodium 1-amino-4((2-isopropylphenyl)amino)-9,10-dioxo-9,10-dihydroanthracene-2-sulfonate.

Optionally, $R_{3'}$ is an isopropyl group. Further optionally or additionally, each of $R_{1'}$, $R_{2'}$, $R_{4'}$, and $R_{5'}$ is a hydrogen atom. Further optionally, the compound is sodium 1-amino-4-((4-isopropylphenyl)amino)-9,10-dioxo-9,10-dihydroanthracene-2-sulfonate.

Optionally, the compound comprises a substituted anthraquinone and has the general formula (ID):

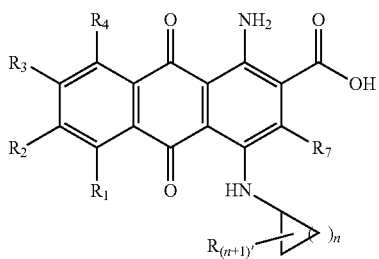

wherein;
n is an integer from 1 to 5;
$R_1$-$R_4$ and $R_7$ are each a hydrogen atom;
X is an alkali metal cation, optionally sodium;
each $R_{(n+1)'}$ is independently selected from at least one of:
  i. a hydrogen atom;
  ii. a heteroatom selected from a halide, optionally fluoride or chloride; an oxygen atom; or an amine, optionally a primary amine;
  iii. a short chain alkyl, alkenyl, or alkynyl group, which can be branched or unbranched, substituted or unsubstituted, linear or cyclic; optionally a short chain alkyl; further optionally an ethyl, propyl, or a butyl group;
  iv. a short chain aza-alkyl, aza-alkenyl, or aza-alkynyl group, which can be branched or unbranched, substituted or unsubstituted, linear or cyclic;
  v. a short chain alkoxyl, alkenoxyl, or alkynoxyl group, which can be branched or unbranched, substituted or unsubstituted, linear or cyclic;
  vi. a short chain thio-alkyl, thio-alkenyl, or thio-alkynyl group, which can be branched or unbranched, substituted or unsubstituted, linear or cyclic;
  vii. a short chain halo-alkyl, halo-alkenyl, or halo-alkynyl group, which can be branched or unbranched, substituted or unsubstituted, linear or cyclic; optionally a fluorinated methyl group; further optionally a trifluoromethyl group;
  viii. a nitrile, hydroxyl or ester group;
  ix. a sulfonate or carboxyl group; and
  x. a tetrazole;
or a pharmaceutically acceptable salt, hydrate, or isomer thereof.

Optionally, n is 4. Further optionally, the compound has the general formula (IE):

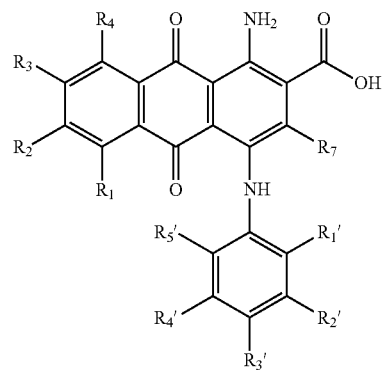

Optionally, $R_{1'}$ and $R_{5'}$, which can be the same or different, are each independently selected from at least one of each of:
  i. a hydrogen atom;
  ii. a heteroatom selected from a halide, optionally fluoride or chloride; or an oxygen atom;
  iii. a short chain alkyl, alkenyl, or alkynyl group, which can be branched or unbranched, substituted or unsubstituted, linear or cyclic; optionally a short chain alkyl; further optionally an ethyl group;
  iv. a short chain alkoxyl, alkenoxyl, or alkynoxyl group, which can be branched or unbranched, substituted or unsubstituted, linear or cyclic; and
  v. a short chain halo-alkyl, halo-alkenyl, or halo-alkynyl group, which can be branched or unbranched, substituted or unsubstituted, linear or cyclic.

Further optionally, $R_{1'}$ and $R_{5'}$, which can be the same or different, are each independently selected from at least one of each of:
  i. a hydrogen atom;
  ii. fluoride;
  iii. a polycyclic group selected from a cycloalkane, cycloalkene, or cycloalkyne;
  iv. a methoxyl group; and
  v. a trifluoromethyl group.

Optionally, $R_{2'}$ and $R_{4'}$, which can be the same or different, are each independently selected from at least one of each of:
  i. a hydrogen atom;
  ii. a heteroatom selected from a halide, optionally fluoride or chloride; an oxygen atom; or an amine, optionally a primary amine;
  iii. a short chain halo-alkyl, halo-alkenyl, or halo-alkynyl group, which can be branched or unbranched, substituted or unsubstituted, linear or cyclic;
  iv. a sulfonate or carboxyl group;
  v. a short chain alkyl, alkenyl, or alkynyl group, which can be branched or unbranched, substituted or unsubstituted, linear or cyclic;
  vi. a short chain alkoxyl, alkenoxyl, or alkynoxyl group, which can be branched or unbranched, substituted or unsubstituted, linear or cyclic;
  vii. a nitrile group;
  viii. a tetrazole; and
  ix. a hydroxyl group.

Further optionally, $R_{2'}$ and $R_{4'}$, which can be the same or different, are each independently selected from at least one of each of:

i. a hydrogen atom;
ii. fluoride;
iii. chloride;
iv. a trifluoromethyl group;
v. a trifluoromethyl group bonded to at least one oxygen atom (—O—CF$_3$);
vi. a methyl group;
vii. an ethyl group;
viii. an isopropyl group;
ix. a tert-butyl group;
x. a cyclopropyl group;
xi. a nitrile group;
xii. a methoxyl group;
xiii. a ethoxyl group;
xiv. an isopropoxyl group;
xv. an amine, optionally a primary amine;
xvi. a polycyclic group selected from a cycloalkane, cycloalkene, or cycloalkyne;
xvii. a benzyl group;
x. a tetrazole; and
xviii. a hydroxyl group.

Optionally, R$_{3'}$ is independently selected from at least one of each of:
i. a hydrogen atom;
ii. a short chain halo-alkyl, halo-alkenyl, or halo-alkynyl group, which can be branched or unbranched, substituted or unsubstituted, linear or cyclic;
iii. a heteroatom selected from a halide, optionally fluoride or chloride; an oxygen atom; or an amine, optionally a primary amine;
iv. a short chain alkyl, alkenyl, or alkynyl group, which can be branched or unbranched, substituted or unsubstituted, linear or cyclic
v. a short chain alkoxyl, alkenoxyl, or alkynoxyl group, which can be branched or unbranched, substituted or unsubstituted, linear or cyclic; and
vi. a nitrile.

Further optionally, R$_{3'}$ is independently selected from at least one of each of:
i. a hydrogen atom;
ii. a trifluoromethyl group;
iii. fluoride;
iv. chloride;
v. a benzyl group;
vi. a methyl group;
vii. a methoxyl group;
viii. an amine, optionally a primary amine; and
ix. a nitrile.

Optionally, R$_{2'}$ is a trifluoromethyl group. Further optionally or additionally, each of R$_{1'}$, and R$_{3'}$-R$_{5'}$ is a hydrogen atom. Further optionally, the compound is sodium 1-amino-9,10-dioxo-4-(3-(trifluoromethyl)phenylamino)-9,10-dihydroanthracene-2-carboxylic acid.

By "dysfunctional" is meant any disturbance resulting in the abnormal functioning of a process, whereby the process no longer follows a conventional functional pattern. The abnormal functioning of the process involves: impaired ion channel activity, the treatment of which comprises enhancement of ion channel activity; and enhanced ion channel activity, the treatment comprising impairment of ion channel activity.

By "impaired ion channel activity" is meant reduced capability of the ion channel to allow passage of ions there through. By "enhancement of ion channel activity" is meant increasing the capability of the ion channel to allow passage of ions there through.

Optionally, the ion channel is a potassium ion channel. Further optionally, the ion channel is a calcium-activated potassium ion channel. Still further optionally, the ion channel is a BK Channel.

Optionally, the disorder is a disorder associated with smooth muscle tone and contraction.

Optionally, the disorder is a disorder associated with smooth muscle tone and contraction in the circulatory system. Further optionally, the disorder is arterial hypertension including decreased blood flow or increased blood pressure. Still further optionally, the disorder is a cardiovascular disorder, optionally myocardial infarction.

Optionally, the disorder is a disorder associated with smooth muscle tone and contraction in the digestive system. Further optionally, the disorder contributes to or manifests as irritable bowel syndrome including incontinence, optionally faecal incontinence; constipation; gastro oesophageal reflux; and impaired gastrointestinal passage.

Optionally, the disorder is associated with smooth muscle tone and contraction in the genitourinary system. Further optionally, the disorder is incontinence, optionally urinary incontinence. Still further optionally, the disorder is erectile dysfunction.

Optionally, the disorder is associated with smooth muscle tone and contraction in the respiratory system. Further optionally, the disorder is associated with constriction of the airway. Still further optionally, the disorder is asthma.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1C depict current recordings over a range of applied voltages from −100 mV to 100 mV at 100 nM Ca$^{2+}$, 1 µM Ca$^{2+}$, and 10 µM Ca$^{2+}$, respectively. FIG. 1D depicts a graph summarizing the results of FIGS. 1A-1C. FIG. 1E illustrates a typical example of an experiment in which single channel recordings were obtained in the presence of 1 µM Ca$^{2+}$ using a voltage ramp protocol before application of a BK channel blocker. FIGS. 1E and 1F demonstrate that addition of Penitrem A abolishes the single channel openings.

FIG. 7A depicts a control trace while FIG. 7B depicts the effect of SR-5-6 (10 μM) on BK channel activity. FIG. 7C illustrates a graph depicting the effects of SR-5-6 on an inside out patch over a range of concentrations. FIG. 7D illustrates a graph depicting the calculated $V_{1/2}$ (the voltage wherein half of the channels in the patch are activated) derived from the data presented in FIG. 7C. These results show that the effects of SR-5-6 on the open probability and $\Delta V_{1/2}$ for BK channels are dose-dependent.

FIG. 8A illustrates a graph depicting the effect of SR-5-69 on BK channel openings over a range of concentrations. FIG. 8B illustrates a graph depicting the calculated $V_{1/2}$ (the voltage wherein half of the channels in the patch are activated) derived from the data presented in FIG. 8A. These results show that the effects of SR-5-69 on the open probability and $\Delta V_{1/2}$ for BK channels are dose-dependent.

FIG. 9A depicts the effect of SR-5-6 on BK channels expressed in Human Embryonic Kidney (HEK) cells transfected to express the pore forming BKα subunit. FIG. 9B illustrates activation curves obtained from rabbit bladder smooth muscle cells in response to increases in $Ca^{2+}$ concentration (100 nM, 1 μM and 10 μM $Ca^{2+}$), wherein the native BK channels were more sensitive to $Ca^{2+}$ compared to the BK alpha subunits shown in FIG. 9A. FIG. 9C illustrates a graph depicting a comparison of the $Ca^{2+}$ sensitivity between smooth muscle cells (black circles), HEK cells expressing the BKα subunit (white squares) and HEK cells co-expressing the $BK_{\beta 1}$ subunit (grey circles) The results show that HEK cells expressing both BKα and $BK_{\beta 1}$ subunits show similar $Ca^{2+}$ dependence as native bladder smooth muscle cells. FIG. 9D illustrates a graph summarizing the mean $\Delta V_{1/2}$ caused by application of 10 μm SR-5-6 in smooth muscle cells, HEK cells expressing the $BK_{\alpha \beta 1}$ subunits and HEK cells only expressing the BKα subunit.

EXAMPLES

Figure 1A:
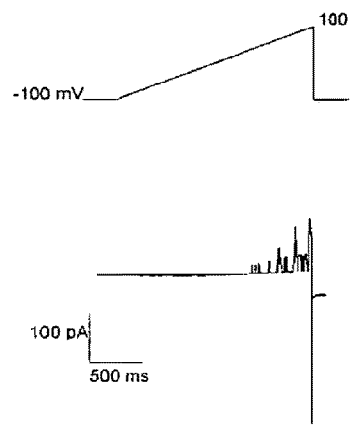
FIGS. 1A-1E illustrate graphs depicting current recordings using inside-out patch clamp technique from isolated smooth muscle cells of a rabbit bladder bathed in Ca$^{2+}$ solution.

All experiments were carried out at 36±1° C., and for the excised patch single channel recordings, the total $Ca^{2+}$ concentration required to give the free $Ca^{2+}$ stated in the text was calculated using Chelator software: (http://www dot organphy dot science dot ru dot nl/chelator/Chelmain dot html).

All experiments were approved by the Dundalk Institute of Technology Animal Care and Use Committee. Tissues were obtained from male and female New Zealand white rabbits immediately after they had been killed by lethal injection of pentobarbitone. The urinary bladder and most proximal 1.5 cm of the urethra was removed and placed in Krebs solution. Strips of bladder tissue, 0.5 cm in width were dissected, cut into 1 $mm^3$ pieces and stored in $Ca^{2+}$-free Hanks' solution for 30 min prior to cell dispersal. Tissue pieces were incubated in dispersal medium containing (per 5 ml) of $Ca^{2+}$-free Hanks' solution: 15 mg collagenase (Sigma type 1A), 1 mg protease (Sigma type XXIV), 10 mg bovine serum albumin (Sigma) and 10 mg trypsin inhibitor (Sigma) for 10-15 min at 37° C. Tissue was then transferred to $Ca^{2+}$-free Hanks' solution and stirred for a further 10-15 min to release single smooth muscle cells. These were plated in Petri dishes containing 100 μM $Ca^{2+}$ Hanks' solution and stored at 4° C. for use within 8 h. During experiments, the dish containing the cells was continuously perfused with Hanks' solution at 36±1° C. Additionally the cell under study was continuously superfused by means of a custom built close delivery system with a pipette of tip diameter 200 μm placed approximately 300 μm from the cell. The high $K^+$ solution in the close delivery system could be switched to a drug-containing solution with a dead space time of less than 5 s.

For whole cell recordings pipettes were pulled from borosilicate glass capillary tubing (1.5 mm outer diameter, 1.17 mm inner diameter; Clark Medical Instruments) to a tip of diameter approximately 1-1.5 μm and resistance of 2-4 Mohms. For single channel recordings, pipettes were pulled from borosilicate glass capillary tubing (1.5 mm outer diameter, 0.8 mm inner diameter; Clark Medical Instruments) and fire polished before use. Voltage clamp commands were delivered via an Axopatch 1D or Axon 200B patch clamp amplifiers (Axon Instruments) and membrane currents were recorded by a 12 bit AD/DA converter (Axodata 1200 or Labmaster, Scientific Solutions) interfaced to an Intel computer running pCLAMP software.

Single Channel Bath Solutions: For Free $Ca^{2+}$ Less than 300 nM:

All values in (mM): KCl, 140. Glucose, 10, EGTA 1 and HEPES, 10. For free $Ca^{2+}$ greater than 300 nM: All values in (mM): KCl, 140. Glucose, 10, H-EDTA 1 and HEPES, 10. The same solution composition is used in the bath as in the patch pipette for these experiments except that the pipette solution contained 100 nM $Ca^{2+}$.

In single channel experiments voltage commands were applied using pClamp ramped potentials. This allowed more efficient measurement of slope conductance and channel activation than conventional step depolarisations. Activation curves were calculated by averaging current responses to 15 potential ramps and dividing each data point of the averaged current by the single channel amplitude at that holding potential, after leakage current correction. The rate of change of the applied ramp potentials were sufficiently slow (100 mVs$^{-1}$) so that the activation curves were not distorted by the time constants of activation or deactivation. This analysis provides a continuous recording of the number of open channels multiplied by the open probability (NPo) over the entire voltage range. To obtain values for the steepness of the voltage-dependent activation and half-maximal activation voltage, activation curves were fitted with Boltzman functions of the form:

$$NPo=n/\{1+\exp[-K(V-V_{1/2})]\}$$

where N is the number of channels in the patch, n is the maximal NPo level, K$^{-1}$ is the steepness of the voltage-dependent activation (change in potential necessary to cause an e-fold increase in activation) and V$_{1/2}$ is the voltage at which there is half-maximal activation. Again, all of the experiments were carried out at 36±1° C.

Figure 1B:
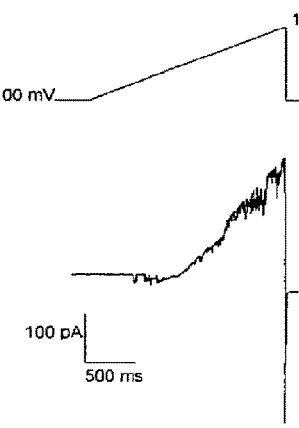
Figure 1C:
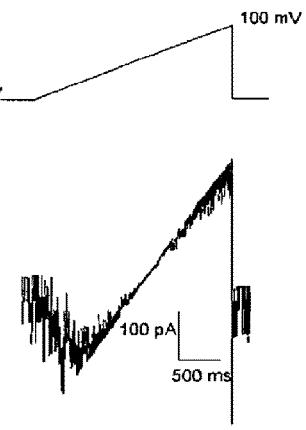
Figure 1D:
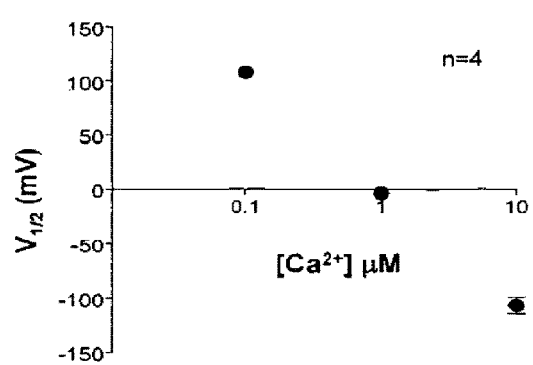
Figure 1E:
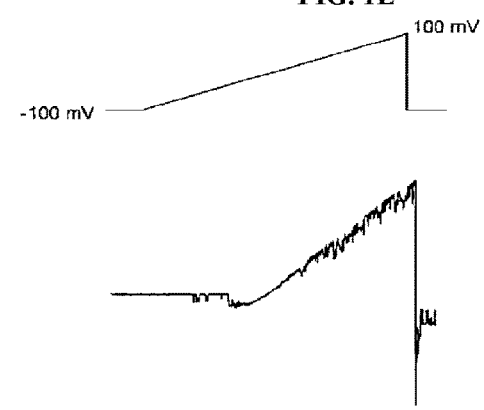
Figure 1F:
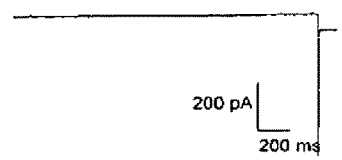
FIG. 1F illustrates an experiment in which single channel recordings were obtained in the presence of 1 µM Ca$^{2+}$ using a voltage ramp protocol after application of Penitrem A (100 nM).
Figure 3:
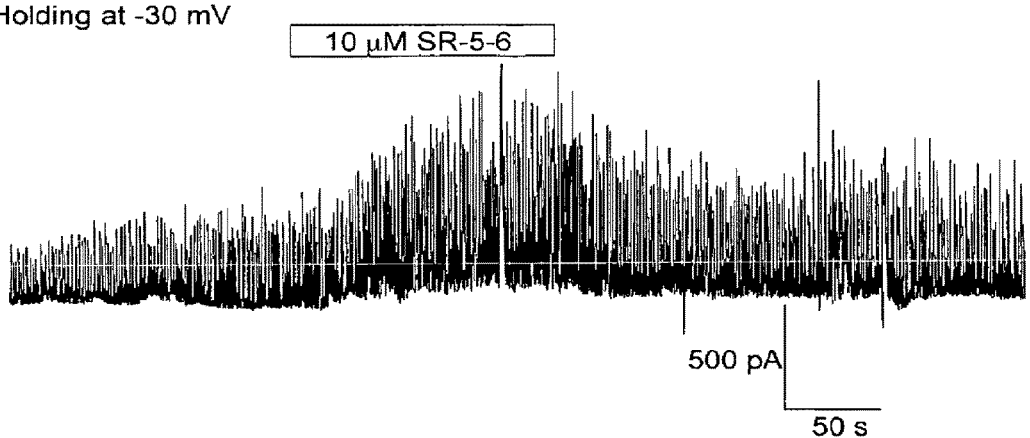
FIG. 3 illustrates a graph depicting the effects of SR-5-6 on spontaneous transient outward currents (STOCs). Isolated smooth muscle cells from rabbit bladder were held under voltage clamps at −30 mV and fired spontaneously active transient outward currents, as a result of activation of BK currents. Application of 10 μM of SR-5-6 increased the amplitude of STOCs.

Example 1: Single Channel Recordings Using Inside-Out Patch Clamp Technique from Isolated Smooth Muscle Cells of the Rabbit Bladder When voltage ramps were applied to inside out patches and the cytosolic face of the patch was bathed in solutions containing 100 nM Ca$^{2+}$, brief single channel openings were only observed at potentials positive to +50 mV. Referring to FIG. 1A, 3 distinct single channel openings which each carried a maximum current of ~30 pA at +100 mV were apparent in this single sweep. These large single channel currents are a hallmark of large conductance K$^+$ (BK) channels. When the Ca$^{2+}$ concentration at the cytosolic face of the patch was increased to 1 µM (FIG. 1B), the number of channels opening increased and the channels activated at more negative potentials. Increasing the Ca$^{2+}$ concentration further to 10 µM as shown in FIG. 1C further enhanced the single channel activity so that up to 4 distinct single channel openings could be observed at potentials negative to –100 mV. Note that the current is inward at voltages negative to 0 mV (reversal potential for K$^+$) and is outward at potentials positive to this. FIG. 1D shows summary data from these experiments, and demonstrates that the voltage at which half of the channels in the patch were maximally activated V$_{1/2}$ (mV) shifted negatively with increasing concentrations of Ca$^{2+}$. In general, a 10 fold change in Ca$^{2+}$ shifted the V$_{1/2}$ by ~100 mV consistent with the idea that these channels comprise the α and β1 subunits of the BK channel. Having established that these channels had a large conductance, were both voltage and calcium sensitive and the currents reversed at the K+ equilibrium potential (0 mV) we next tested the effect of the selective BK channel blocker Penitrem A in a separate series of experiments. FIG. 1E shows a typical example of an experiment in which single channel recordings were obtained in the presence of 1 µM Ca$^{2+}$ using a voltage ramp protocol (upper panel) before (lower panel) application of the blocker. In this example, the BK channels activated at negative potentials (~–50 mV) reversed at 0 mV and were macimally activated at positive potentials. FIG. 1F shows the recording from same patch of membrane after application of the selective BK channel blocker Penitrem A (100 nM). As FIGS. 1E and 1F suggest, Penitrem A abolished the single channel openings.

These data characterize the current under investigation, and are consistent with the characteristics that would be expected from a large conductance BK channel, showing that the current being activated is the current elicited by opening of BK channels.

Example 2: Isolated Cells Using Perforated Patch with Sodium 1-Amino-9,10-Dioxo-4-(Phenylamino)-9,10-Dihydroanthracene-2-Sulfonate. (Acid Blue 25)

Isolated smooth muscle cells are dispersed as described in Example 1. Currents were recorded using the perforated patch configuration of the whole cell patch clamp technique (Rae et al., 1991). The cell membrane was perforated using the antibiotic amphotericin B (600 µg·ml$^{-1}$). Other methods including the preparation of patch pipettes and recording of currents are as described in Example 1.

K Perforated Patch Solution:

All values in (mM): KCl, 132.96. MgCl$_2$.6H$_2$0, 1. EGTA, 0.5 and HEPES, 10. Standard Hank's solution is used to bathe the cells in these experiments. Isolated smooth muscle cells from rabbit urethra we held at –60 mV. The test protocol involved stepping from –60 mV to –80 mV for 500 msecs, and then stepping the voltage up in +10 mV increments to +50 mV before returning to the holding potential of –60 mV. This is diagrammatically shown in FIG. 2.

Figure 2:
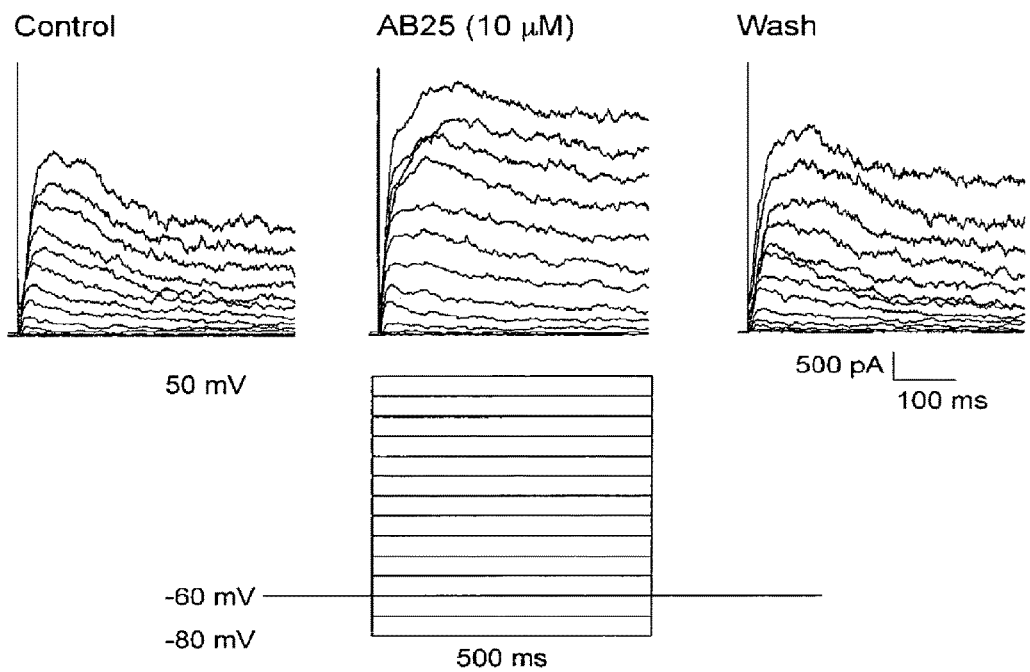
FIG. 2 illustrates graphs depicting current recordings using the perforated patch configuration of the whole cell patch clamp technique with Acid Blue 25. The Control panel depicts a family of outward currents elicited in response to the voltage protocol in the lower panel. The AB25 (10 µM) panel depicts the potentiating effects of Acid Blue 25 (10 µM) on the outward BK current in response to the voltage protocol in the lower panel. The Wash panel depicts the effect of Acid Blue 25 (10 µM) can be washed out, returning the currents to control levels.

The Control panel in FIG. 2 shows a family of outward currents recorded using the perforated patch configuration and elicited under in response to the voltage protocol shown in the lower panel. These noisy outward currents are consistent with currents being carried through large conductance BK channels. The centre panel of FIG. 2 shows the potentiating effects of Acid Blue 25 (10 µM) on the outward BK current in response to the same voltage steps. The right hand panel shows the effect of Acid Blue 25 can be washed out returning the currents to control levels. Acid Blue 25 (10 µM) enhances the amplitude of the BK current compared to control, an effect that is reversible upon wash-out.

Example 3: Sodium 1-Amino-9,10-Dioxo-4-(3-(Trifluoromethyl)Phenylamino)-9,10-Dihydroanthracene-2-Sulfonate (SR-5-6) Potentiates STOCs (Spontaneous Transient Outward Currents) Recorded Using the Perforated Patch Clamp Technique from Isolated Smooth Muscle Cells from the Rabbit Bladder Using the perforated patch clamp techniques described in Example 2, the effects of the compounds of the present invention were observed on spontaneous transient outward currents (STOCs). In this experiment, isolated smooth muscle cells from rabbit bladder were held under voltage clamp at –30 mV and fired spontaneously active transient outward currents, as a result of activation of BK currents.

As seen in FIG. 3, application of 10 µM SR-5-6 increased the amplitude of STOCs, recorded using perforated patch clamp techniques. This effect was reversible on wash-out. These data indicate that SR-5-6 activates BK channels in spontaneously active smooth muscle cells when the cells are held at –30 mV.

Example 4: Dose-Response of Sodium 1-Amino-9, 10-Dioxo-4-(3-(Trifluoromethyl)Phenylamino)-9,10-Dihydroanthracene-2-Sulfonate (SR-5-6) at Single Voltage Step—Perforated Patch Clamp Recordings from Isolated Smooth Muscle Cells from the Rabbit Bladder Using the perforated patch clamp techniques described in Example 2, isolated smooth muscle cells from the rabbit bladder were held at –60 mV and stepped to 0 mV for 500 msec to elicit the BK current.

Figure 4:
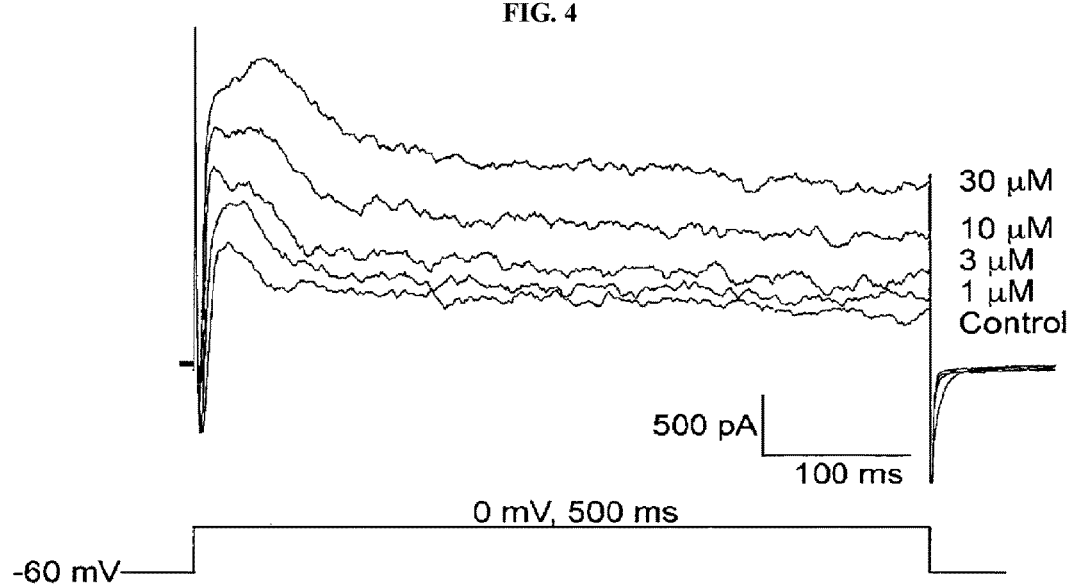
FIG. 4 illustrates a graph depicting the dose response of SR-5-6 at a single voltage step as observed through perforated patch clamp recordings from isolated smooth muscle cells from a rabbit bladder. The graph demonstrates that the activation of BK channels by SR-5-6 occurs in a dose-dependent manner when the cell is held at −60 mV and then stepped to 0 mV for 500 msec.

As seen in FIG. 4, the outward current elicited during perforated patch recordings using this protocol is potentiated in a dose dependent manner, using the compound sodium 1-amino-9,10-dioxo-4-(3-(trifluoromethyl)phenylamino)-9,10-dihydroanthracene-2-sulfonate (SR-5-6). These data demonstrate that the activation of BK channels by SR-5-6 occurs in a dose-dependent manner when the cell is exposed to the above protocol.

Example 5: Effects of Sodium 1-Amino-9,10-Dioxo-4-(3-(Trifluoromethyl)Phenylamino)-9,10-Dihydroanthracene-2-Sulfonate (SR-5-6) on L-Type Calcium Channel—Perforated Patch Clamp Recordings from Isolated Smooth Muscle Cells of the Rabbit Bladder, Using $Cs^+$ in the Pipette Solution to Block BK Channels Using methods described above herein, the patch pipette solution was altered to allow for measurement of inward L-type calcium currents which although present in earlier studies are not visible due to the overwhelming size of the outward BK current. By replacing $K^+$ with $Cs^+$ ions, the outward current is now blocked and a prominent inward current carried by Calcium is present. This is the L-type calcium ion channel currents allowing calcium into the cells.
Pipette Solution:
All values in (mM): CsCl, 132.96. $MgCl_2.6H_2O$, 1. EGTA, 0.5 and HEPES, 10.

Figure 5:
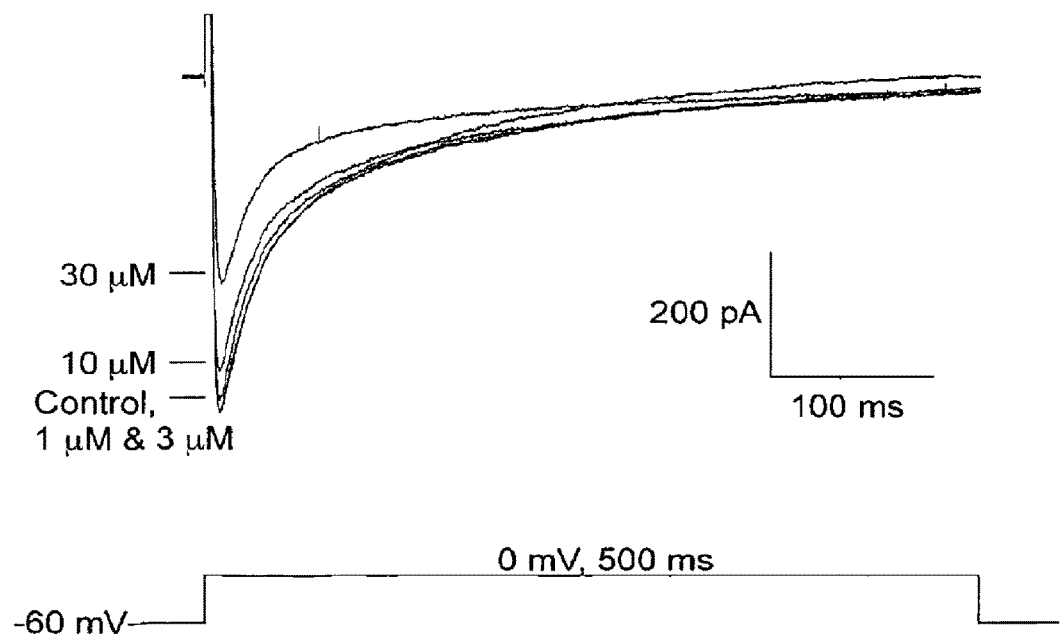
FIG. 5 illustrates a graph depicting the effect of SR-5-6 on L-type calcium channels as observed through perforated patch clamp recordings from isolated smooth muscle cells from a rabbit bladder. Isolated cells were held at −60 mV and stepped to 0 mV for 500 msec. A $Cs^+$ solution was added and the measured inward L-type calcium current was reduced in amplitude in the presence of SR-5-6 in a dose-dependent manner.

With reference to FIG. 5, isolated smooth muscle cells from the rabbit bladder were held at −60 mV and stepped to 0 mV for 500 ms. Pipette solutions contained $Cs^+$ to block outward $K^+$ currents. An inward L-type calcium current measured using perforated patch clamp technique, is reduced in amplitude in the presence of SR-5-6 in a dose-dependent manner. As the BK channels are known to be activated both by a change in voltage but also by an increase in intracellular $Ca^{2+}$ ions, it is important to rule out a mechanism of action whereby SR-5-6 was activating BK channels by increasing the influx of $Ca^{2+}$ through activation of voltage gated $Ca^{2+}$ channels and subsequent $Ca^{2+}$ activation of BK channels. This experiment shows that the increase in outward BK current with SR-5-6 observed previously (FIGS. 3-4) is not due to activation of L-type calcium currents and subsequent influx of calcium, rather that there is a modest inhibitory effect on influx of $Ca^{2+}$ through these channels.

Example 6: Ramp Protocol Showing Sodium 1-Amino-9,10-Dioxo-4-(3-(Trifluoromethyl)Phenylamino)-9,10-Dihydroanthracene-2-Sulfonate (SR-5-6) Effects—Single Channel Recordings Using Inside-Out Patch Clamp Technique from Isolated Smooth Muscle Cells of the Rabbit Bladder Using the single channel inside-out patch clamp technique described in Example 1, recordings of BK single channels in patches of membrane from isolated smooth muscle cells from rabbit bladder, were obtained using the inside out patch clamp configuration. The patches were held at a potential of −100 mV and voltage ramps were then applied from −100 mV up to +100 mV over 2 s.

Figure 6:
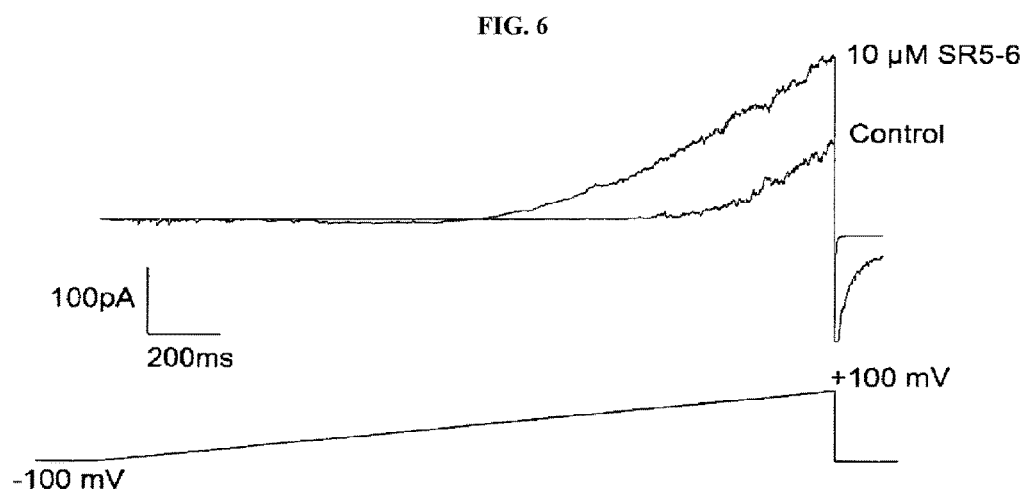
FIG. 6 illustrates a graph depicting the effect of SR-5-6 on BK single channel recordings using inside-out patch clamp technique from isolated smooth muscle cells of a rabbit bladder bathed in $Ca^{2+}$ solution (200 nM). The patches were held at a potential of −100 mV and the voltage ramps were applied from −100 mV to +100 mV over 2 seconds. The upper trace depicts the current measurement in the presence of SR-5-6 (10 μM) while the lower trace depicts the control measurement. The graph demonstrates that BK channels activate at lower potential in the presence of SR-5-6.

As seen in FIG. 6, when $Ca^{2+}$ was buffered to ~200 nM, the BK channels began to activate at potentials positive to +50 mV. When the same voltage ramp was reapplied in the presence of 10 μM SR5-6 the threshold voltage for activation of the channels was shifted ~100 mV in the hyperpolarising direction.

The results of this experiment show that the current evoked in response to the voltage ramp protocol shifted the activation potential to a much more negative potential. This is consistent with the idea that this compound activates BK channels since having a greater population of BK channels open would cause activation of an outward BK current at more negative potentials in the physiologically relevant range of potentials (i.e., negative to 0 mV). In addition, the amount of current elicited throughout the duration of the ramp is larger in the presence of SR-5-6 than in control conditions. Finally, since these data were collected from an inside-out patch, a situation where the compound is applied to the inside of the cell membrane, it seems probable that the compound is activating the BK channel on this small patch of membrane from the inside surface of the cell. Consequently one can conclude that SR-5-6 activates BK channels in an isolated patch of membrane, by directly opening the ion channel from the inside surface of the cell. However, given the data from whole cell recordings we can also conclude that the compound can activate BK channels when presented on exterior surface (outside) of the cell.

Example 7: Cumulative Data Showing Sodium 1-Amino-9,10-Dioxo-4-(3-(Trifluoromethyl)Phenylamino)-9,10-Dihydroanthracene-2-Sulfonate (SR-5-6) on Ramps—Single Channel Recordings Using Inside-Out Patch Clamp Technique from Isolated Smooth Muscle Cells of the Rabbit Bladder Using the single channel inside out patch clamp technique, described in Example 1, voltage ramps were used to observe openings of BK channels, as described in Example 6.

Figure 7A:
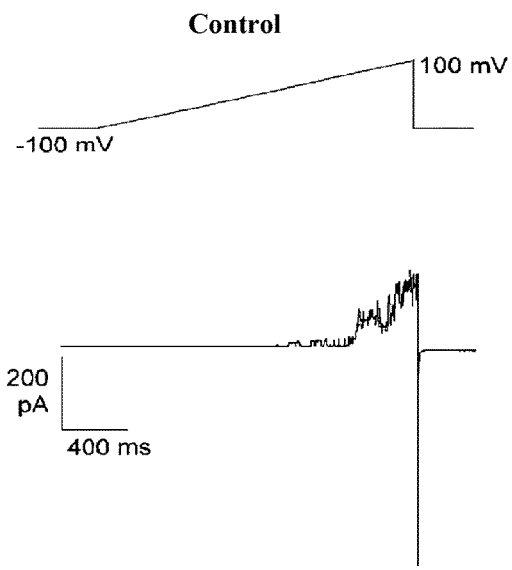
FIGS. 7A-7D illustrate graphs depicting the effect of SR-5-6 on the opening of BK channels.
Figure 7B:
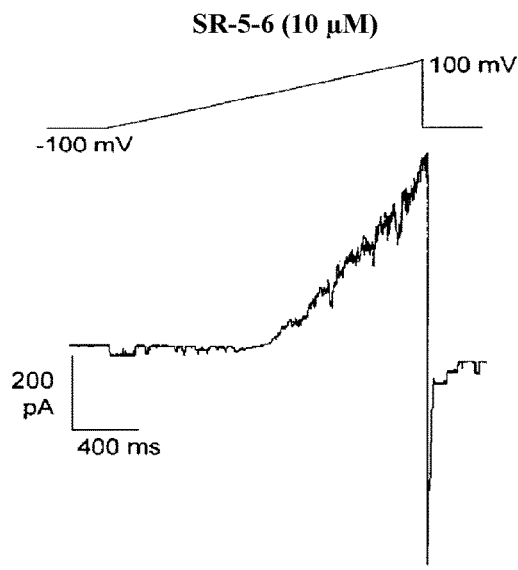
Figure 7C:
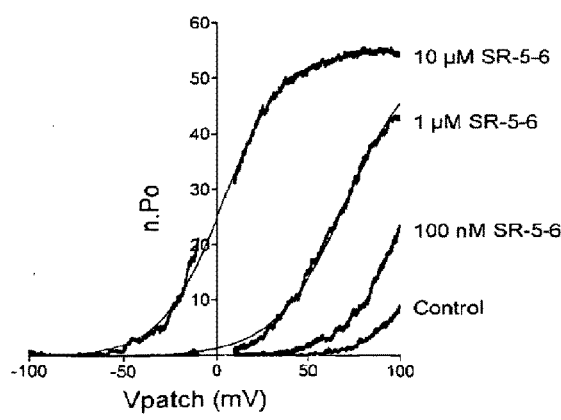
Figure 7D:
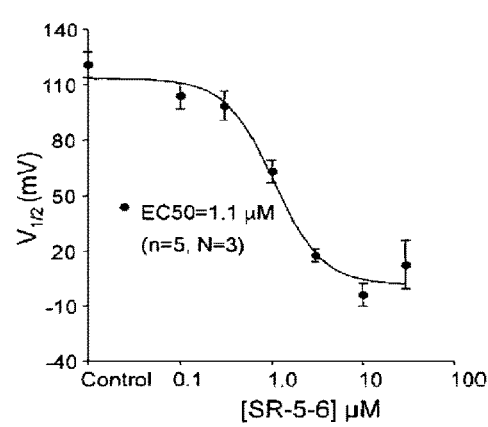

Referring to FIG. 7A shows the control trace using the ramp protocol as described above herein. FIG. 7B shows the effect of 10 μM SR-5-6 on the channel activity, as seen previously. FIG. 7C shows a typical example of the effects of SR-5-6 on an inside out patch. To obtain these data, the average single channel currents were obtained from 15 voltage ramp sweeps under control conditions and then in the presence of each concentration of the drug. The mean currents were corrected for driving force by dividing the current by the single channel amplitude at each potential. Consequently, activation curves similar to those shown in FIG. 7C can be obtained. When these data are fitted with a Boltzmann relationship, the voltage at which half of the channels in the patch are activated can be calculated ($V_{1/2}$). These data show that the effects of SR-5-6 are dose-dependent and shift the activation of the channels towards more physiologically relevant membrane potentials. FIG. 7D shows a summary plot of five experiments in which the mean activation $V_{1/2}$ of the channels was plotted under control conditions (~200 nM $Ca^{2+}$) and in the presence of increasing concentrations of SR-5-6. The error bars show the standard error of the mean for each data point.

These data show conclusively that the effects of SR-5-6 on the open probability and $\Delta V_{1/2}$ for BK channels are dose-dependent, which is a critical factor in the development of drug candidates.

Example 8: Comparing Structure Function Relationships Using Single Channel Recordings of Inside-Out Patches from Isolated Smooth Muscle Cells of the Rabbit Bladder To compare the effect of a variety of chemical substitutions on the BK channels, experiments were carried out using voltage ramps applied to inside out patches which were bathed with either 188 nM free $Ca^{2+}$ or 100 nM free $Ca^{2+}$ on their cytosolic face. Patches were held at −100 mV and ramped through to +100 mV and each sweep was repeated 15 times. The same protocol was repeated after the patch was incubated in 1 µM $Ca^{2+}$. The patch was then returned to 100 nM $Ca^{2+}$ containing solutions and 10 µM of the drug of interest was applied. After a maximal effect was observed, the voltage ramps were reapplied to the patch in the presence of the drug. Data from each series of voltage ramp was then averaged. These mean currents were corrected for driving force by dividing the current by the single channel amplitude at each potential. When these data were fitted with a Boltzmann relationship, the voltage at which half of the channels in the patch were activated could be calculated ($V_{1/2}$). The observed shift in activation ($\Delta V_{1/2}$) under control conditions and in the presence of each drug was obtained by subtracting the $V_{1/2}$ in control and the $V_{1/2}$ in drug. Table 1 and Table 2 show a summary data series of experiments in which the average $\Delta V_{1/2}$ of each molecule is compared.

TABLE 1

The effect of applying 10 µM of compounds on $\Delta V_{1/2}$ according to a first aspect of the present invention

| Compound | $\Delta V_{1/2}$ (mV) in 100 nm $Ca^{2+}$ |
|---|---|
| SR-5-18 | −23.2 |
| SR-5-14 | −24.2 |
| SR-5-8 | −24.24 |
| SR-5-15 | −28.4 |
| Acid Blue 25 | −51.0 |
| SR-5-26 | −53.5 |
| SR-5-12 | −54.1 |
| Acid Blue 62 | −54.37 |
| SR-5-32 | −61.1 |
| SR-5-37 | −77.8 |
| SR-5-28 | −83.2 |
| SR-5-34 | −84.0 |
| SR-5-31 | −87.1 |
| SR-5-6 | −90.9 |
| SR-5-40 | −97.8 |
| SR-5-44 | −145.4 |

TABLE 2

The effect compounds on $\Delta V_{1/2}$ of activation.

| Compound (Concentration) | $\Delta V_{1/2}$ (mV) in 100 nm $Ca^{2+}$ |
|---|---|
| SR-5-53 (10 µM) | −44.1 |
| SR-5-63 (10 µM) | −113.1 |
| SR-5-64 (10 µM) | −87.6 |
| SR-5-65 (10 µM) | −116.2 |
| SR-5-68 (10 µM) | −120.0 |
| SR-5-69 (1 µM) | −101.6 |
| SR-5-76 (10 µM) | −94.9 |
| SR-5-88 (10 µM) | −98.8 |
| SR-5-94 (10 µM) | −60.0 |
| SR-5-72 (10 µM) | −103.8 |
| SR-5-96 (10 µM) | −84.8 |
| SR-5-97 (10 µM) | −78.5 |
| SR-5-98 (10 µM) | −120.0 |
| SR-5-99 (10 µM) | −83.4 |
| SR-5-66 (10 µM) | −53.4 |

Example 9

Using the single channel inside out patch clamp technique described in Example 1, voltage ramps were used to observe openings of BK channels, as described in Example 6.

Figure 8A:
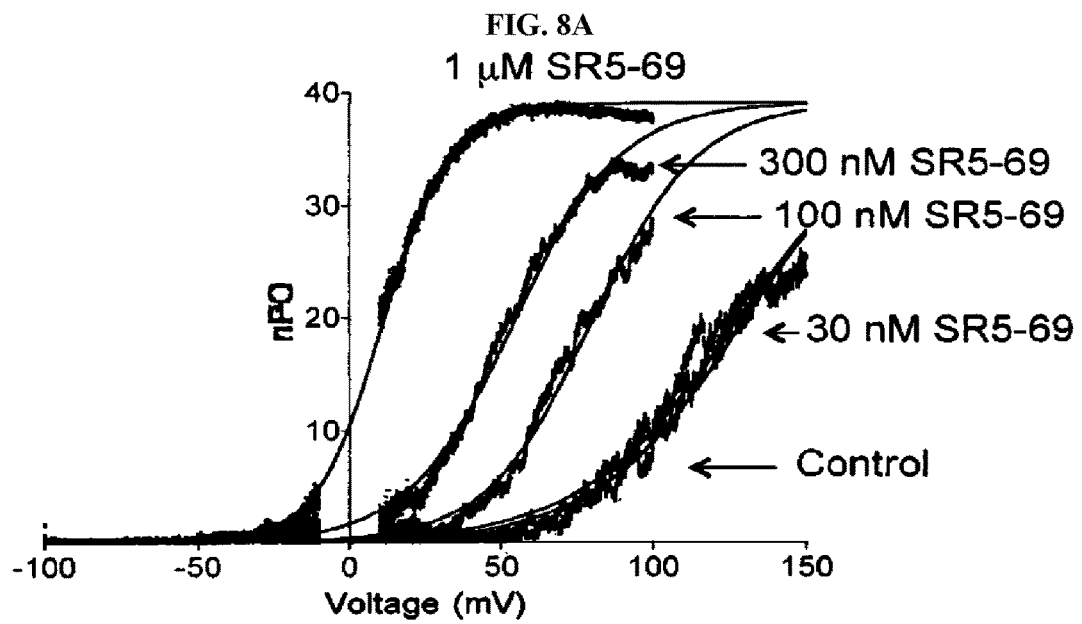
FIGS. 8A-8B illustrate graphs depicting the effect of SR-5-69 on the opening of BK channels.
Figure 8B:
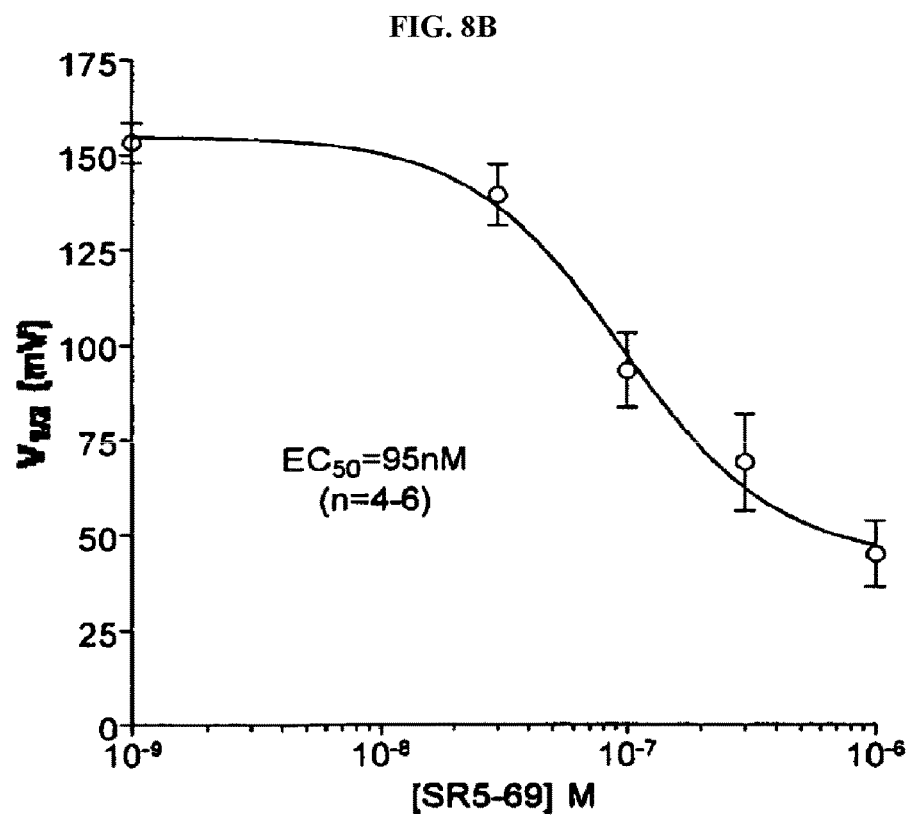

Referring to FIG. 8A shows the control trace (black) obtained using the ramp protocol as described above herein. To obtain these data, the average single channel currents were obtained from voltage ramp sweeps under control conditions and then in the presence of each concentration of the drug. The mean currents were corrected for driving force by dividing the current by the single channel amplitude at each potential. Consequently, activation curves similar to those shown in FIG. 7C can be obtained. When these data are fitted with a Boltzmann relationship, the voltage at which half of the channels in the patch are activated can be calculated ($V_{1/2}$). These data show that the effects of SR-5-69 are dose-dependent and shift the activation of the channels towards more physiologically relevant membrane potentials. Application of SR-5-69 (30 nM) produced a very small shift in the activation $V_{1/2}$ in this example. However, increasing the concentration of SR-5-69 to 100 nM, 300 nM and 1 µM caused a concentration dependent shift in the activation curve in the hyperpolarising direction, such that at the highest concentration used (1 µM), SR-5-69 shifted the $V_{1/2}$ in excess of −100 mV, to approximately +5 mV. FIG. 8B-shows a summary graph in which the mean $V_{1/2}$ was plotted against each concentration of the drug for n=4-6 patches containing BK channels. The error bars show the standard error of the mean for each data point.

When these data were fitted with the Langmuir equation, the fit yielded a mean $EC_{50}$ of 95 nM, consistent with the idea that this molecule was a potent and efficacious opener of BK channels.

Example 10: BK Openers Stimulate BK Channels Expressed in HEK Cells

Figure 9A:
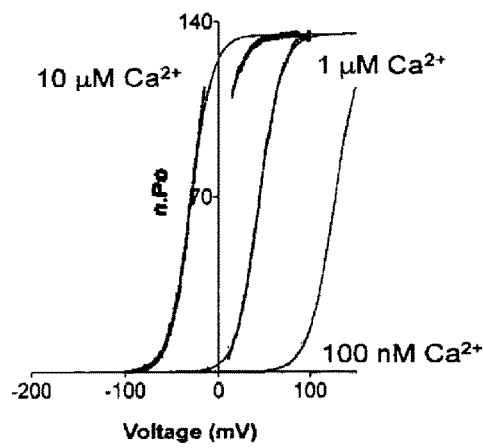
FIGS. 9A-9D illustrate graphs depicting the effect of the compounds of the invention on BK channels in cells other than bladder smooth muscle cells.

To demonstrate the effect of the compounds of the present invention on BK channels in cells other than bladder smooth muscle, the effects of SR-5-6 on BK channels expressed in Human Embryonic Kidney (HEK) cells were examined using the same technique and protocols described above. As FIG. 9A suggests, large currents could be recorded from HEK cells transfected to express the pore forming BKα subunit. These currents were activated by depolarisation and by increasing the $Ca^{2+}$ concentration at the cytosolic face of the channel ($[Ca^{2+}]i$. As expected, the currents recorded from BKα subunit expressing HEK cells were less sensitive to $[Ca^{2+}]i$ than the channels in native smooth muscle cells (FIG. 9A & FIG. 9C). Consequently, higher $[Ca^{2+}]l$ shifted the $V_{1/2}$ of BK channels recorded from bladder smooth muscle more negatively than those recorded from HEK cells, expressing only the BKα subunit. This difference in $Ca^{2+}$ sensitivity between BK channels recorded in smooth muscle cells (FIG. 9C, black circles) and HEK cells expressing the BKα subunit (FIG. 9C, white squares) has been well established and is due to the presence of the regulatory BKβ$_1$ subunit in smooth muscle cells. Consequently we examined the effect of co-expressing the BKα subunit with the BKβ$_1$ subunit in HEK cells. As the grey circles in FIG. 9C show, the $Ca^{2+}$ sensitivity of the HEK cells expressing BKαβ$_1$ subunits, was practically identical to that of the channels recorded from native bladder smooth muscle cells.

Figure 9B:
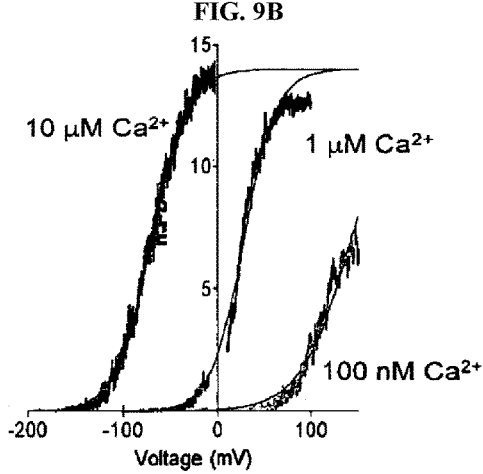
Figure 9C:
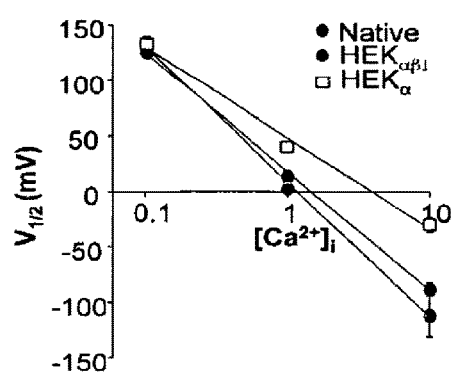

FIG. 9B illustrates activation curves obtained from rabbit bladder smooth muscle cells in response to increases in $Ca^{2+}$ concentration (100 nM, 1 µM and 10 µM $Ca^{2+}$), wherein the native BK channels were more sensitive to $Ca^{2+}$ compared to the BK alpha subunits shown in FIG. 9A.

Figure 9D:
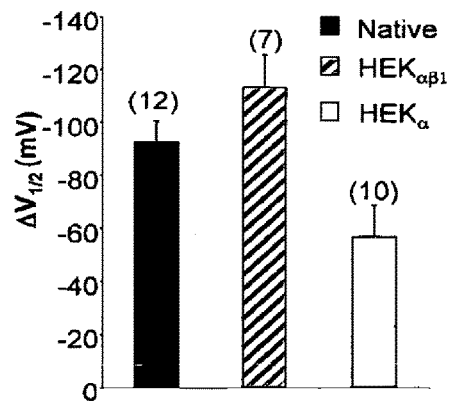

Having established these two cell lines, the effects of 10 µM SR-5-6 on HEK cells expressing either BKα subunits alone or co-expressing BKαβ$_1$ subunits were examined and its effects with those on native bladder smooth muscle cells were compared. FIG. 9D shows a summary barchart in which the mean shift in activation $V_{1/2}$ (delta $V_{1/2}$) caused by application of 10 µM SR-5-6, was compared in native bladder smooth muscle cells (black bar), HEK cells expressing the BKαβ$_1$ subunits (hashed bar) and HEK cells expressing the BKα subunit alone (white bar). The vertical lines represent the SEM and the numbers in parentheses represent the number of experiments per group. As the data suggests, SR-5-6 shifted the activation $V_{1/2}$ of channels recorded from all three cell types, but it was less effective at shifting the $V_{1/2}$ in cells expressing only the BKα subunits (white bar). These data suggest that SR-5-6 can activate BK channels when they are expressed in HEK cells and is consistent with the idea that this molecule can activate BK channels, irrespective of what cell type they are present in.

Conclusion

Basilen blue had been characterized as a moderately potent BK channel activator when applied to the inside of the membrane of smooth muscle cell, shifting the activation voltage for the BK channel into the negative range (K. D. Cotton et al.).

It has been demonstrated herein that a series of truncated derivatives of basilen blue can be synthesized; and the effects each thereof have been investigated on the inside out patches on rabbit smooth muscle cells. It has been shown that the commercially available dye, Acid Blue 25, synthesized from bromaminic acid, shifted the $V_{1/2}$ by −56 mV. However, Bromaminic acid was also tested; and it strongly decreased the activity on BK channel, in fact, it showed an inhibitory effect.

Screening of different analogues of anilinoanthraquinone, each having a different substituent on the benzene ring (D ring) of the Acid Blue 25 was also undertaken. In the present invention, the introduction of the hydrophobic substituent either in the ortho-position of the benzene ring (D ring), for example, ethyl [SR-5-96], isopropyl [SR-5-98] or in the meta-position, for example, trifluoromethyl [SR-5-6], isopropyl [SR-5-63], benzyl [SR-5-68] and tert-butyl [SR-5-76] produced BK channel agonists. However, the incorporation of hydrophobic substituent at para-position in D ring, for example, ethyl [SR-5-97], isopropy [SR-5-99], benzyl [SR-5-37] furnished BK channel openers.

The replacement of the benzene ring (D ring) in SR-5-64 by indane led to similar potent compound like SR-5-6. Moreover, when the benzene ring was replaced by β-tetralin [SR-5-69] or β-naphthalene [SR-5-72], the dramatic increase in the activity was observed. SR-5-69 (1 µM) and SR-5-72 (1 µM) shifted the $V_{1/2}$ by 110 mV and 93 mV respectively. However, when the benzene ring was substituted with α-naphthalene ring [SR-5-66], the potency was dropped substantially. But, the replacement of the benzene ring with α-tetralin ring [SR-5-65] provided a potent BK channel activator.

On the other hand, introducing a polar substituent in the meta-position of the benzene ring, for example, $SO_3H$ [SR-5-18] decreases the activity dramatically.

Without being bound by theory, the above examples suggest that a hydrophobic group particularly at the ortho- and meta-position of the phenyl ring is desirable for BK channel activation. However, the activity was not altered by substituting the sulfonate group in the C ring of SR-5-6 with its isostere carboxylate group [SR-5-88]. But, replacement of the sulfonate moiety by a H-atom at C-ring in Acid Blue 25 (1-amino-9,10-dioxo-4-(phenylamino)-9,10-dihydroanthracene-2-sulfonate) completely abolished the activity, indicating the importance of a negatively charged group at the C-2 position.

These observations suggest that an appropriate hydrophobic region in the benzene ring (D ring) of anilinoanthraquinone and the sulfonate or carboxylate functionality of ring C are desirable for BK channel-opening activity (Scheme 1). The present SAR study based on $V_{1/2}$ data showed that the Acid Blue 25 structure is a new scaffold for BK channel openers.

Scheme 1: Structure-Activity Relationship of anilinoanthraquinone analogues as BK channel activators.

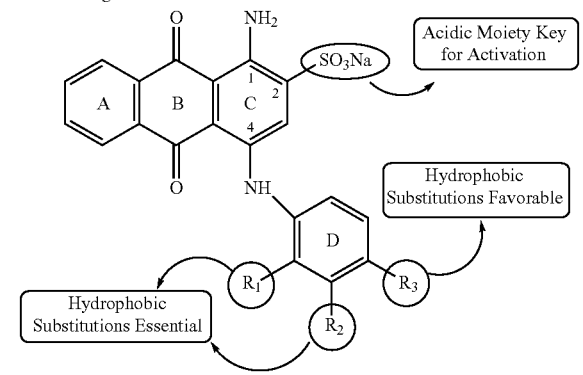

Accordingly, the present invention provides compounds useful as ion channel modulators that specifically and potently open BK channels in rabbit bladder smooth muscle cells and HEK cells transfected to allow production of BK channels. These compounds shift the activation of the BK channels in a hyperpolarising direction, towards physiological potentials.

Materials & Methods

General Details $^1$H-NMR and $^{13}$C-NMR data were collected at 300 K using a Bruker AMX 400 MHz NMR spectrometer at 400 MHz ($^1$H), or 100 MHz ($^{13}$C), respectively. Residual DMSO (δ 2.50) was used as internal references for $^1$H NMR spectra. The data reported as chemical shift ($δ_H$ ppm), relative integral, multiplicity (s=singlet, br=broad, d=doublet, t=triplet, q=quartet, m=multiplet), coupling constant (J Hz), and assignment. Solvent peak for DMSO (δ 39.7) was used as internal reference for $^{13}$C NMR spectra. High Resolution Mass Spectra (HRMS) was recorded by the School of Chemistry and Chemical Biology, University College Dublin using a Micromass/Waters LCT instrument. Microwave reactions were carried out using a CEM Focused™ Microwave Synthesis type Discover® apparatus. Reactions were monitored by thin layer chromatography (TLC), which was performed on aluminum sheets pre-coated with Silica gel 60 $F_{254}$ (Merck). Column-chromatography separations were performed using Merck Kieselgel 60 (0.040-0.063 mm). The columns were usually eluted with various combinations of ethyl acetate-methanol mixtures. All reagents were obtained from commercial sources and used as received.

Synthetic Procedure of Ullmann Coupling Reaction

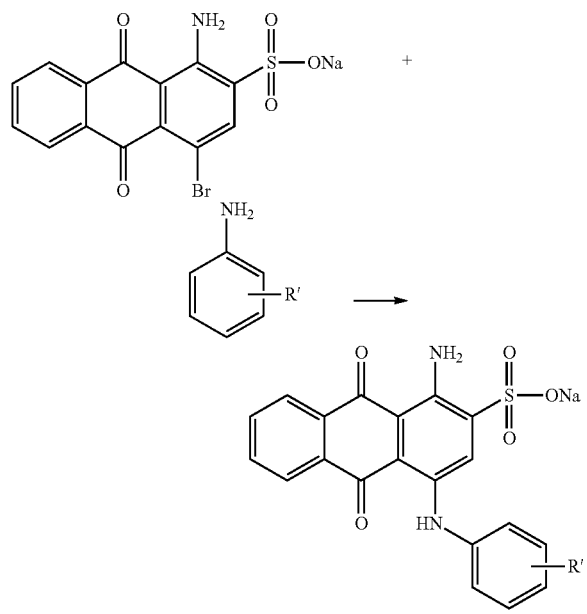

Procedure A:

Bromaminic acid sodium salt (0.2 g, 0.495 mmol), the suitable aniline derivative (0.99 mmol), copper powder (31 mg, 0.495 mmol) and buffer solution of $Na_2HPO_4$ (0.2 M, 3 mL) and $NaH_2PO_4$ (0.12 M, 5 mL) was mixed in a 35 mL microwave reaction vial. Reaction vial was capped and irradiated with microwave reactor (70 W-80 W) for 5-20 minutes at 100-120° C. Reaction mixture was cooled to room temperature and filtered. Filtrate was extracted with ethyl acetate (40 mL×3) and washed with water. Combined organic layer was dried over anhydrous sodium sulfate and concentrated under reduced pressure. The resulting crude product was loaded on silica gel column and eluted with 2%-4% methanol in ethyl acetate mixture to furnish the corresponding pure anilinoanthraquinone derivative as a blue solid.

TABLE 3

Isolated yields of material judged homogeneous by TLC and NMR.

| Compound | Yield (%)[a] |
|---|---|
| Acid Blue 25 | — |
| SR-5-6 | 75 |
| SR-5-11 | 43 |
| SR-5-12 | 83 |
| SR-5-13 | 30 |
| SR-5-14 | 36 |
| SR-5-15 | 51 |
| SR-5-18 | 25 |
| SR-5-23 | 41 |
| SR-5-26 | 82 |
| SR-5-28 | 65 |
| SR-5-31 | 79 |
| SR-5-34 | 76 |
| SR-5-37 | 68 |
| SR-5-40 | 79 |
| SR-5-44 | 75 |
| SR-5-46 | 62 |
| SR-5-47 | 44 |
| SR-5-48 | 62 |
| SR-5-53 | 65 |
| SR-5-61 | 70 |
| SR-5-63 | 75 |
| SR-5-64 | 66 |
| SR-5-65 | 68 |
| SR-5-66 | 48 |
| SR-5-68 | 72 |
| SR-5-69 | 76 |
| SR-5-76 | 68 |
| SR-5-88 | 55 |
| SR-5-91 | 47 |
| SR-5-94 | 53 |
| SR-5-72 | 67 |
| SR-5-96 | 64 |
| SR-5-97 | 78 |
| SR-5-98 | 69 |
| SR-5-99 | 75 |

[a] Yields reported here are isolated yields of material judged homogeneous by TLC and NMR.

Procedure B:

Bromaminic acid sodium salt (0.2 g, 0.495 mmol), sodium carbonate (42 mg, 0.396 mmol), copper sulfate (16 mg, 0.1 mmol) and the suitable aniline or amine derivative were mixed in 5 mL water. Reaction mixture was stirred at 65° C. for 1 h and then refluxed gently at 105° C. for 5 h. The reaction mixture was then cooled to room temperature and filtered. Filtrate was extracted with ethyl acetate (40 mL×3) and washed with water. Combined organic extract was dried over anhydrous sodium sulfate and concentrated under reduced pressure. The resulting crude product was loaded on silica gel column and eluted with 3% methanol in ethyl acetate to obtain the corresponding anilinoanthraquinone derivative as a blue powder.

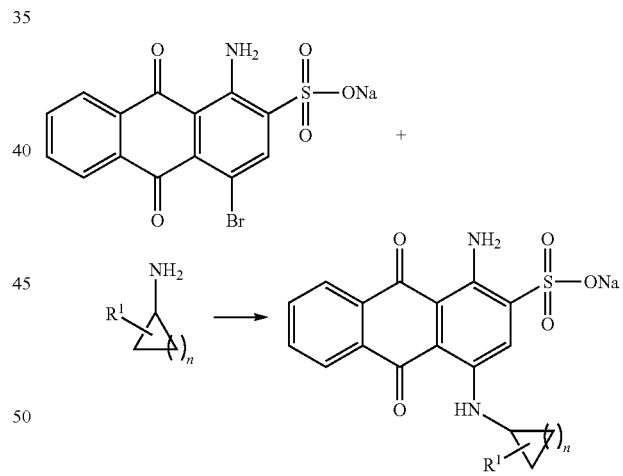

TABLE 4 isolated yields of material judged homogeneous by TLC and NMR

| n | Compound | Yield (%)[a] |
|---|---|---|
| 1 | SR-5-10 | 39 |
| 2 | SR-5-20 | 40 |
| 3 | SR-5-8 | 47 |
| 4 | Acid blue 62 | — |
| 5 | SR-5-32 | 49[b] |

[a] Yields reported here are isolated yields of material judged homogeneous by TLC and NMR.
[b] Reaction was performed following the procedure B.

SR-5-6: sodium 1-amino-9,10-dioxo-4-(3-(trifluoromethyl)phenylamino)-9,10-dihydroanthracene-2-sulfonate.

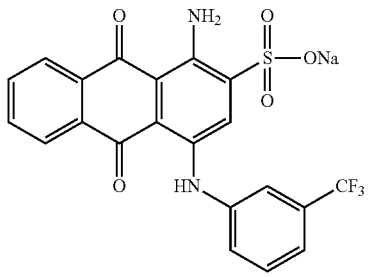

$R_f$: 0.4 (20% methanol in ethyl acetate).
$^1$H NMR (400 MHz, DMSO-d$_6$): δ 11.80 (s, 1H), 10.02 (brs, 1H), 8.24 (dd, J=7.2, 13.2 Hz, 2H), 8.04 (s, 1H), 7.85 (m, 2H), 7.65-7.56 (m, 3H), 7.48 (d, J=7.6 Hz, 1H).
$^{13}$C NMR (100 MHz, DMSO-d$_6$): δ 183.2, 182.1, 144.6, 142.2 (2C), 140.8, 138.8, 134.0, 133.4, 133.3, 132.9, 130.7 (2C), 126.0, 125.9, 125.6, 122.8, 119.9, 118.4, 113.1, 109.6.
HRMS (ES): m/z for C$_{21}$H$_{12}$N$_2$O$_5$F$_3$S [M−Na$^+$], calcd. 461.0419. found 461.0440.

SR-5-8: sodium 1-amino-4-(cyclopentylamino)-9,10-dioxo-9,10-dihydroanthracene-2-sulfonate.

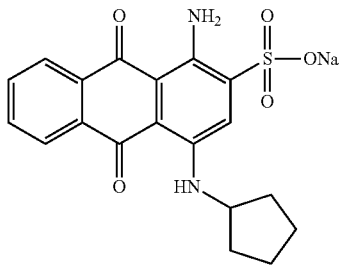

$R_f$: 0.4 (20% methanol in ethyl acetate).
$^1$H NMR (400 MHz, DMSO-d$_6$): δ 10.86 (d, J=6.8 Hz, 1H), 10.13 (brs, 1H), 8.27-8.23 (m, 2H), 7.82 (s, 1H), 7.81-7.79 (m, 2H), 4.14-4.10 (m, 1H), 2.14-2.07 (m, 2H), 1.80-1.68 (m, 6H).
$^{13}$C NMR (100 MHz, DMSO-d$_6$): δ 181.5, 180.7, 144.7, 143.4, 143.0, 133.9 (2C), 132.5, 132.4, 125.8, 125.7, 121.6, 109.0, 108.7, 53.3, 33.6 (2C), 23.6 (2C).
HRMS (ES): m/z for C$_{16}$H$_{18}$N$_2$O$_6$NaS [M+H$^+$], calcd. 409.0834. found 409.0850.

SR-5-10: sodium 1-amino-4-(cyclopropylamino)-9,10-dioxo-9,10-dihydroanthracene-2-sulfonate.

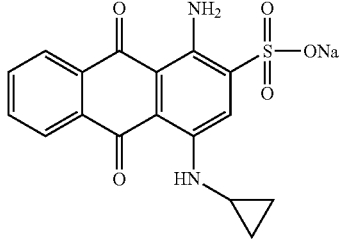

$R_f$: 0.4 (20% methanol in ethyl acetate).
$^1$H NMR (400 MHz, DMSO-d$_6$): δ 10.51 (d, J=2.4 Hz, 1H), 10.09 (brs, 1H), 8.27-8.24 (m, 1H), 8.22-8.20 (m, 1H), 8.17 (s, 1H), 7.82-7.80 (m, 2H), 2.80-2.67 (m, 1H), 0.94-0.90 (m, 2H), 0.65-0.62 (m, 2H).
$^{13}$C NMR (100 MHz, DMSO-d$_6$): δ 181.7, 181.4, 145.8, 143.4, 143.2, 133.9, 133.7, 132.6 (2C), 125.9, 125.7, 122.1, 109.2, 109.1, 24.1, 7.63 (2C).
HRMS (ES): m/z for C$_{17}$H$_{13}$N$_2$O$_6$Na$_2$S [M+Na$^+$], calcd. 403.0341. found 403.0359.

SR-5-11: sodium 1-amino-4-(2,6-difluorophenylamino)-9,10-dioxo-9,10-dihydroanthracene-2-sulfonate.

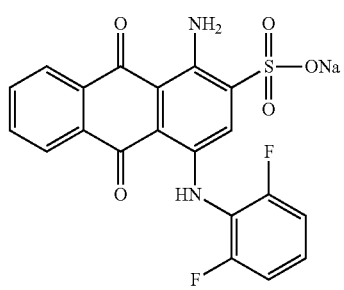

$R_f$: 0.4 (20% methanol in ethyl acetate).
$^1$H NMR (400 MHz, DMSO-d$_6$): δ 11.52 (s, 1H), 9.98 (brs, 1H), 8.30-8.27 (m, 2H), 7.89-7.86 (m, 2H), 7.43-7.30 (m, 4H).
$^{13}$C NMR (100 MHz, DMSO-d$_6$): δ 183.5, 182.1, 158.91-156.45 (d, J=246.0 Hz), 158.87-156.40 (d, J=247.0 Hz), 144.1, 142.7, 140.6, 134.1, 133.5, 133.3, 132.9, 127.4, 126.1, 126.0, 121.8, 115.91-115.75 (d, J=16.0 Hz), 112.6, 112.4, 111.5, 109.2.
HRMS (ES): m/z for C$_{20}$H$_{11}$N$_2$O$_6$F$_2$S [M−Na$^+$], calcd. 429.0357. found 429.0348.

SR-5-12: sodium 1-amino-4-(2-methoxyphenylamino)-9,10-dioxo-9,10-dihydroanthracene-2-sulfonate.

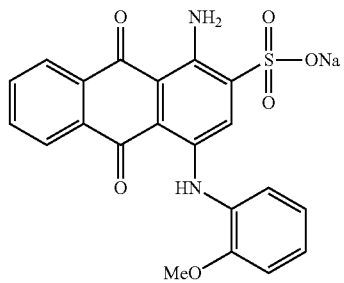

$R_f$: 0.3 (20% methanol in ethyl acetate).
$^1$H NMR (400 MHz, DMSO-d$_6$): δ 11.94 (s, 1H), 10.12 (brs, 1H), 8.30-8.27 (m, 2H), 7.97 (s, 1H), 7.88-7.83 (m, 2H), 7.30 (d, J=7.2 Hz, 1H), 7.20-7.17 (m, 2H), 7.05-7.01 (m, 1H), 3.88 (s, 3H).

SR-5-13: sodium 4-(3,5-bis(trifluoromethyl)phenylamino)-1-amino-9,10-dioxo-9,10-dihydroanthracene-2-sulfonate.

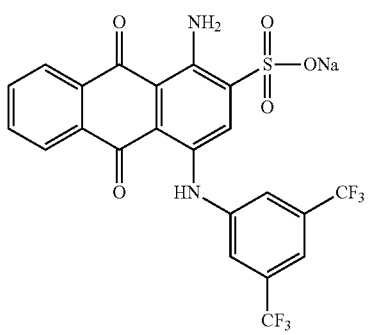

$R_f$: 0.4 (20% methanol in ethyl acetate).
$^1$H NMR (400 MHz, DMSO-$d_6$): δ 11.39 (s, 1H), 9.87 (brs, 1H), 8.21-8.14 (m, 2H), 7.98 (s, 1H), 7.85-7.78 (m, 4H), 7.62 (s, 1H).
HRMS (ES): m/z for $C_{22}H_{11}N_2O_6F_6S$ [M−Na$^+$], calcd. 529.0293. found 529.0292.
SR-5-14: sodium 1-amino-4-(3,5-difluorophenylamino)-9,10-dioxo-9,10-dihydroanthracene-2-sulfonate.

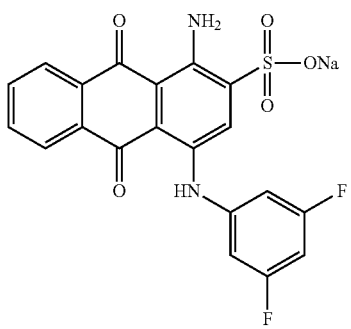

$R_f$: 0.4 (20% methanol in ethyl acetate).
$^1$H NMR (400 MHz, DMSO-$d_6$): δ 11.55 (s, 1H), 9.98 (brs, 1H), 8.28-8.22 (m, 2H), 8.08 (s, 1H), 7.91-7.84 (m, 2H), 7.49 (brs, 1H), 7.00 (dd, J=2.4, 9.4 Hz, 2H), 6.96-6.90 (m, 1H).
HRMS (ES): m/z for $C_{20}H_{11}N_2O_6F_2S$ [M−Na$^+$], calcd. 429.0357. found 429.0370.
SR-5-15: sodium 1-amino-4-(3-fluorophenylamino)-9,10-dioxo-9,10-dihydroanthracene-2-sulfonate.

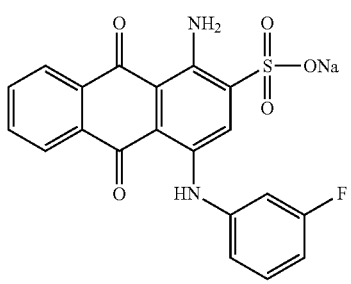

$R_f$: 0.4 (20% methanol in ethyl acetate).
$^1$H NMR (400 MHz, DMSO-$d_6$): δ 11.83 (s, 1H), 10.05 (brs, 1H), 8.28-8.23 (m, 2H), 8.06 (s, 1H), 7.89-7.82 (m, 2H), 7.49-7.43 (m, 1H), 7.17-7.11 (m, 2H), 6.99 (dt, J=2.4, 8.2 Hz, 1H).
$^{13}$C NMR (100 MHz, DMSO-$d_6$): δ 183.0, 182.0, 164.05-161.63 (d, J=242.0 Hz), 144.5, 142.3, 141.6, 139.2, 134.1, 133.4, 133.3, 132.9, 131.2, 126.1, 126.0, 123.0, 118.1, 112.6, 110.52-110.31 (d, J=21.0 Hz), 109.4, 109.0.
HRMS (ES): m/z for $C_{20}H_{12}N_2O_6FS$ [M−Na$^+$], calcd. 411.0451. found 411.0464.
SR-5-18: sodium 1-amino-9,10-dioxo-4-(3-sulfophenylamino)-9,10-dihydroanthracene-2-sulfonate.

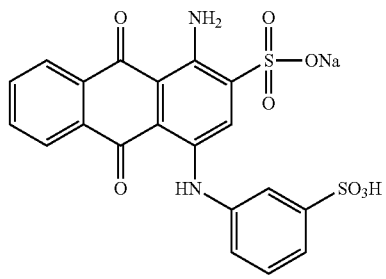

$R_f$: 0.2 (25% methanol in ethyl acetate).
$^1$H NMR (400 MHz, DMSO-$d_6$): δ 12.05 (s, 1H), 10.11 (brs, 1H), 8.30-8.28 (m, 2H), 8.00 (s, 1H), 7.88-7.85 (m, 2H), 7.46-7.39 (m, 3H), 7.25 (td, J=2.4, 7.1 Hz, 1H).
SR-5-20: sodium 1-amino-4-(cyclobutylamino)-9,10-dioxo-9,10-dihydroanthracene-2-sulfonate.

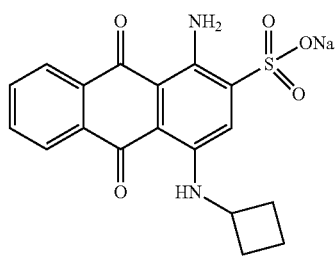

$R_f$: 0.4 (20% methanol in ethyl acetate).
$^1$H NMR (400 MHz, DMSO-$d_6$): δ 10.74 (d, J=6.0 Hz, 1H), 10.10 (brs, 1H), 8.27-8.23 (m, 2H), 7.83-7.80 (m, 2H), 7.64 (s, 1H), 7.41 (brs, 1H), 4.22 (m, 1H), 2.49-2.46 (m, 2H), 2.06-1.96 (m, 2H), 1.90-1.83 (m, 2H).
HRMS (ES): m/z for $C_{18}H_{16}N_2O_6S$ [M−Na$^+$], calcd. 371.0702. found 371.0692.
SR-5-23: sodium 1-amino-4-(3-fluoro-5-(trifluoromethyl)phenylamino)-9,10-dioxo-9,10-dihydroanthracene-2-sulfonate.

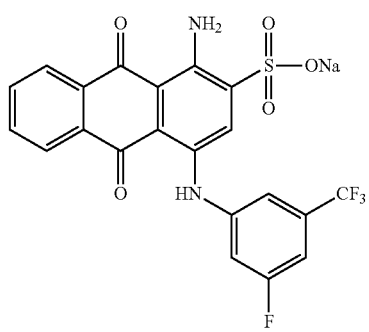

$R_f$: 0.4 (20% methanol in ethyl acetate).

¹H NMR (400 MHz, DMSO-d₆): δ 11.51 (s, 1H), 9.96 (brs, 1H), 8.25 (dd, J=3.2, 15.6 Hz, 2H), 8.06 (s, 1H), 7.95-7.84 (m, 2H), 7.47 (s, 1H), 7.42 (d, J=10.8 Hz, 1H), 7.32 (d, J=8.0 Hz, 1H).

HRMS (ES): m/z for $C_{21}H_1N_2O_5F_4S$ [M−Na⁺], calcd. 479.0325. found 479.0344.

SR-5-26: sodium 4-(m-toluidino)-1-amino-9,10-dioxo-9,10-dihydroanthracene-2-sulfonate.

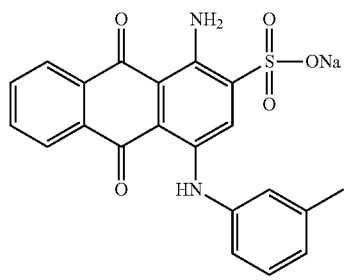

$R_f$: 0.4 (20% methanol in ethyl acetate).

¹H NMR (400 MHz, DMSO-d₆): δ 12.05 (s, 1H), 10.12 (brs, 1H), 8.27 (dt, J=2.4, 6.8 Hz, 2H), 8.04 (s, 1H), 7.87-7.82 (m, 2H), 7.54 (brs, 1H), 7.34 (t, J=7.6 Hz, 1H), 7.11 (s, 1H), 7.07 (dd, J=7.6, 24.4 Hz, 2H), 2.35 (s, 3H).

SR-5-28: sodium 1-amino-4-(4-fluoro-3-(trifluoromethyl)phenylamino)-9,10-dioxo-9,10-dihydroanthracene-2-sulfonate.

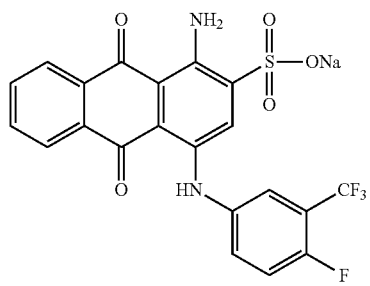

$R_f$: 0.4 (20% methanol in ethyl acetate).

¹H NMR (400 MHz, DMSO-d₆): δ 11.73 (s, 1H), 9.99 (brs, 1H), 8.21 (dd, J=7.2, 15.2 Hz, 2H), 7.91 (s, 1H), 7.86-7.80 (m, 2H), 7.67-7.63 (m, 2H), 7.57 (t, J=10.0 Hz, 1H).

¹³C NMR (100 MHz, DMSO-d₆): 183.0, 182.0, 156.37-153.87 (d, J=250.0 Hz), 144.4, 142.3, 139.5, 136.7, 136.6, 134.0, 133.3 (2C), 132.9, 129.0, 126.0, 125.9, 122.4, 121.3, 121.2, 118.50-118.28 (d, J=22.0 Hz), 112.7, 109.5.

HRMS (ES): m/z for $C_{21}H_{11}N_2O_5F_4Na_2S$ [M+Na⁺], calcd. 525.0120. found 525.0107.

SR-5-31: sodium 1-amino-4-(3-ethylphenylamino)-9,10-dioxo-9,10-dihydroanthracene-2-sulfonate.

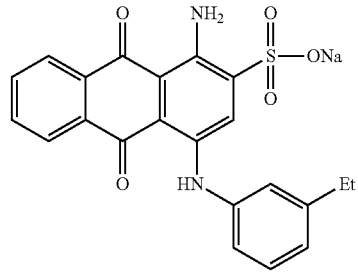

$R_f$: 0.4 (20% methanol in ethyl acetate).

¹H NMR (400 MHz, DMSO-d₆): δ 12.07 (s, 1H), 10.13 (brs, 1H), 8.31-8.23 (m, 2H), 8.08 (s, 1H), 7.87-7.81 (m, 2H), 7.36 (t, J=7.6 Hz, 1H), 7.14 (s, 1H), 7.08 (dd, J=8.0, 20.2 Hz, 2H), 2.64 (ABq, J=7.6 Hz, 2H), 1.22 (t, J=7.6 Hz, 3H).

¹³C NMR (100 MHz, DMSO-d₆): 182.3, 181.8, 145.6, 144.3, 142.6, 140.9, 139.1, 134.1, 133.5, 133.1, 132.7, 129.5, 126.0, 125.9, 124.0, 122.8, 122.5, 120.3, 111.3, 109.1, 28.1, 15.5.

HRMS (ES): m/z for $C_{22}H_{17}N_2O_6Na_2S$ [M+Na⁺], calcd. 467.0654. found 467.0666.

SR-5-32: sodium 1-amino-4-(cycloheptylamino)-9,10-dioxo-9,10-dihydroanthracene-2-sulfonate.

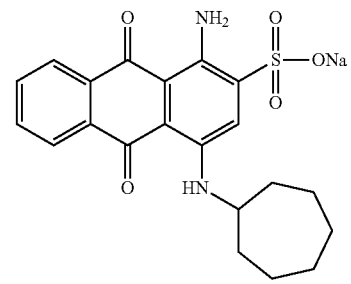

$R_f$: 0.4 (20% methanol in ethyl acetate).

¹H NMR (400 MHz, DMSO-d₆): δ 10.95 (d, J=7.6 Hz, 1H), 10.18 (brs, 1H), 8.27-8.24 (m, 2H), 7.81-7.79 (m, 2H), 7.75 (s, 1H), 3.91-3.86 (m, 1H), 2.02-1.96 (m, 2H), 1.70-1.59 (m, 10H).

¹³C NMR (100 MHz, DMSO-d₆): δ 181.4, 180.6, 144.2, 143.5, 143.0, 134.0, 133.9, 132.4, 132.3, 125.8, 125.7, 121.4, 109.1, 108.7, 52.1, 34.7 (2C), 27.6 (2C), 23.5 (2C).

HRMS (ES): m/z for $C_{21}H_{21}N_2O_6Na_2S$ [M+Na⁺], calcd. 459.0967. found 459.0970.

SR-5-34: sodium 1-amino-9,10-dioxo-4-(3-(trifluoromethoxy)phenylamino)-9,10-dihydroanthracene-2-sulfonate.

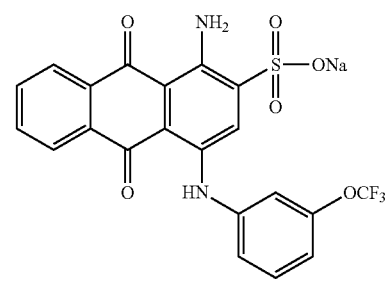

$R_f$: 0.4 (20% methanol in ethyl acetate).

$^1$H NMR (400 MHz, DMSO-d$_6$): δ 11.78 (s, 1H), 10.02 (brs, 1H), 8.27-8.22 (m, 2H), 8.07 (s, 1H), 7.89-7.82 (m, 2H), 7.54 (t, J=8.0 Hz, 1H), 7.31-7.28 (m, 2H), 7.12 (d, J=8.4 Hz, 1H).

$^{13}$C NMR (100 MHz, DMSO-d$_6$): δ 183.2, 182.1, 149.3, 144.6, 142.2, 141.7, 138.7, 134.0, 133.4, 133.3, 132.9, 131.2 (20), 126.0 (20), 123.0, 120.6, 115.6, 114.3, 113.1, 109.6.

HRMS (ES): m/z for C$_{21}$H$_{12}$N$_2$O$_6$F$_3$Na$_2$S [M+Na$^+$], calcd. 523.0164. found 523.0179.

SR-5-37: sodium 1-amino-4-(4-benzylphenylamino)-9,10-dioxo-9,10-dihydroanthracene-2-sulfonate.

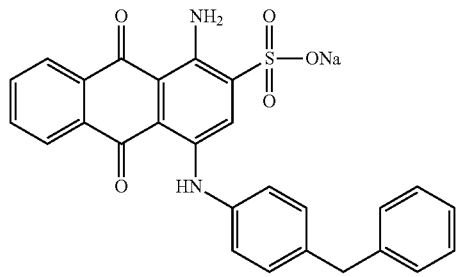

R$_f$: 0.4 (20% methanol in ethyl acetate).

$^1$H NMR (400 MHz, DMSO-d$_6$): δ 12.07 (s, 1H), 10.11 (brs, 1H), 8.29-8.26 (m, 2H), 8.00 (s, 1H), 7.88-7.81 (m, 2H), 7.34-7.20 (m, 9H), 3.98 (s, 2H).

HRMS (ES): m/z for C$_{27}$H$_{19}$N$_2$O$_6$Na$_2$S [M+Na$^+$], calcd. 529.0810. found 529.0812.

SR-5-40: sodium 1-amino-4-(4-chloro-3-(trifluoromethyl)phenylamino)-9,10-dioxo-9,10-dihydroanthracene-2-sulfonate.

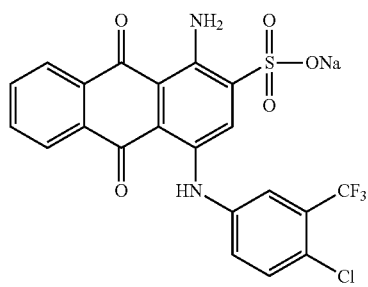

R$_f$: 0.4 (20% methanol in ethyl acetate).

$^1$H NMR (400 MHz, DMSO-d$_6$): δ 11.61 (s, 1H), 9.96 (brs, 1H), 8.24-8.17 (m, 2H), 8.00 (s, 1H), 7.87-7.80 (m, 2H), 7.72 (s, 1H), 7.71 (d, J=12.0 Hz, 1H), 7.54 (dd, J=2.8, 8.8 Hz, 1H).

HRMS (ES): m/z for C$_{21}$H$_{11}$N$_2$O$_6$F$_3$Na$_2$SCl [M+Na$^+$], calcd. 540.9825. found 540.9824.

SR-5-44: sodium 1-amino-4-(4-methyl-3-(trifluoromethyl)phenylamino)-9,10-dioxo-9,10-dihydroanthracene-2-sulfonate.

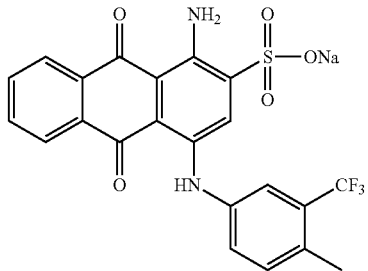

R$_f$: 0.4 (20% methanol in ethyl acetate).

$^1$H NMR (400 MHz, DMSO-d$_6$): δ 11.85 (s, 1H), 10.05 (brs, 1H), 8.25-8.20 (m, 2H), 7.97 (s, 1H), 7.86-7.80 (m, 2H), 7.55 (s, 1H), 7.49-7.44 (m, 2H), 2.45 (s, 3H).

HRMS (ES): m/z for C$_{22}$H$_{14}$N$_2$O$_6$F$_3$Na$_2$S [M+Na$^+$], calcd. 521.0371. found 521.0382.

SR-5-46: sodium 1-amino-4-(3-chlorophenylamino)-9,10-dioxo-9,10-dihydroanthracene-2-sulfonate.

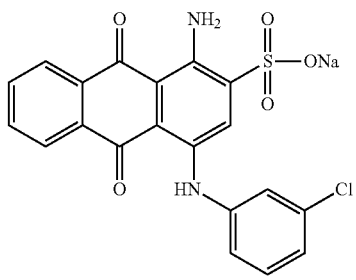

R$_f$: 0.4 (20% methanol in ethyl acetate).

$^1$H NMR (400 MHz, DMSO-d$_6$): δ 11.79 (s, 1H), 10.04 (brs, 1H), 8.28-8.23 (m, 2H), 8.03 (s, 1H), 7.89-7.83 (m, 2H), 7.45 (t, J=8.0 Hz, 1H), 7.36 (t, J=2.0 Hz, 1H), 7.26-7.20 (m, 2H).

SR-5-47: sodium 1-amino-4-(3-cyanophenylamino)-9,10-dioxo-9,10-dihydroanthracene-2-sulfonate.

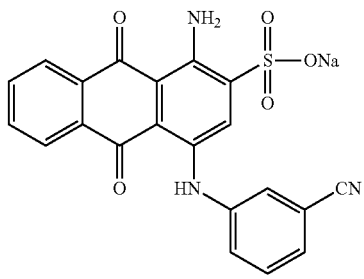

R$_f$: 0.3 (20% methanol in ethyl acetate).

$^1$H NMR (400 MHz, DMSO-d$_6$): δ 11.72 (s, 1H), 10.01 (brs, 1H), 8.28-8.23 (m, 2H), 7.99 (s, 1H), 7.90-7.83 (m, 2H), 7.74 (s, 1H), 7.62-7.56 (m, 3H).

HRMS (ES): m/z for C$_{21}$H$_{12}$N$_3$O$_6$Na$_2$S [M+Na$^+$], calcd. 464.0293. found 464.0280.

SR-5-48: sodium 1-amino-4-((3-methoxy-5-(trifluoromethyl)phenyl)amino)-9,10-dioxo-9,10-dihydroanthracene-2-sulfonate

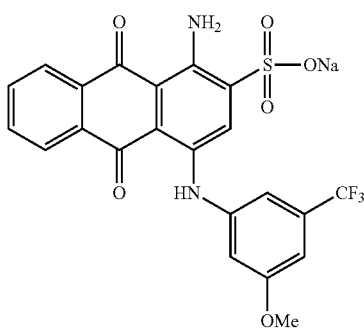

R$_f$: 0.4 (20% methanol in ethyl acetate).
$^1$H NMR (400 MHz, DMSO-d$_6$): δ 11.74 (s, 1H), 10.01 (brs, 1H), 8.29-8.24 (m, 2H), 8.09 (s, 1H), 7.91-7.84 (m, 2H), 7.50 (brs, 1H), 7.18 (s, 1H), 7.14 (s, 1H), 6.98 (s, 1H), 3.86 (s, 3H).
HRMS (ES): m/z for C22H14N2O6F3Na2S [M+Na+], calcd. 537.0320. found 537.0342.

SR-5-53: sodium 1-amino-4-((3-hydroxyphenyl)amino)-9,10-dioxo-9,10-dihydroanthracene-2-sulfonate

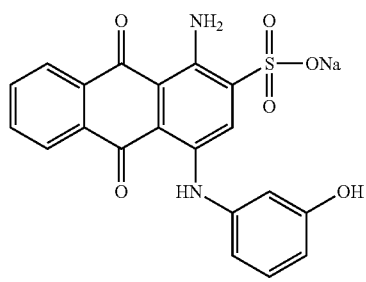

R$_f$: 0.3 (20% methanol in ethyl acetate).
$^1$H NMR (400 MHz, DMSO-d$_6$): δ 11.99 (s, 1H), 10.12 (brs, 1H), 9.68 (s, 1H), 8.28-8.24 (m, 2H), 8.08 (s, 1H), 7.87-7.81 (m, 2H), 7.52 (brs, 1H), 7.24 (t, J=8.0 Hz, 1H), 6.72-6.62 (m, 3H).

SR-5-61: sodium 1-amino-4-(2-methoxy-5-(trifluoromethyl)phenylamino)-9,10-dioxo-9,10-dihydroanthracene-2-sulfonate

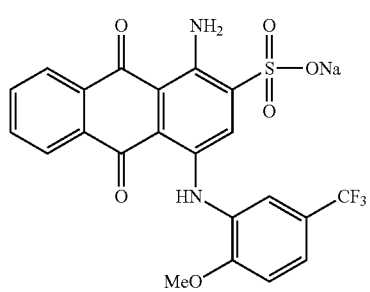

R$_f$: 0.4 (20% methanol in ethyl acetate).
$^1$H NMR (400 MHz, DMSO-d$_6$): δ 11.82 (s, 1H), 10.04 (brs, 1H), 8.28-8.25 (m, 2H), 7.98 (s, 1H), 7.89-7.84 (m, 2H), 7.60 (d, J=1.6 Hz, 1H), 7.50 (d, J=8.8 Hz, 1H), 7.34 (d, J=8.8 Hz, 1H), 3.97 (s, 3H).
HRMS (ES): m/z for C$_{22}$H$_{14}$N$_2$O$_6$F$_3$Na$_2$S [M+Na$^+$], calcd. 537.0320. found 537.0344.

SR-5-63: sodium 1-amino-4-((3-isopropylphenyl)amino)-9,10-dioxo-9,10-dihydroanthracene-2-sulfonate

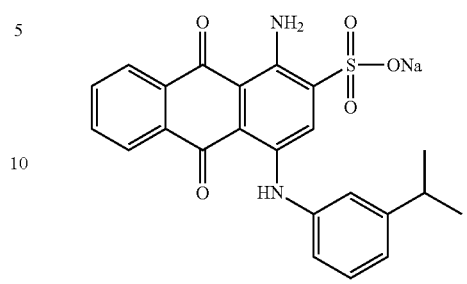

R$_f$: 0.4 (20% methanol in ethyl acetate).
$^1$H NMR (400 MHz, DMSO-d$_6$): δ 12.10 (s, 1H), 10.13 (brs, 1H), 8.31-8.25 (m, 2H), 8.10 (s, 1H), 7.88-7.82 (m, 2H), 7.54 (brs, 1H), 7.37 (t, J=8.0 Hz, 1H), 7.18 (s, 1H), 7.10 (t, J=7.6 Hz, 2H), 2.96-2.89 (m, 1H), 1.25 (d, J=6.8 Hz, 6H).
HRMS (ES): m/z for C$_{23}$H$_{16}$N$_2$O$_6$Na$_2$S [M+Na$^+$], calcd. 481.0810. found 481.0816.

SR-5-64: sodium 1-amino-4-((2,3-dihydro-1H-inden-5-yl)amino)-9,10-dioxo-9,10-dihydroanthracene-2-sulfonate

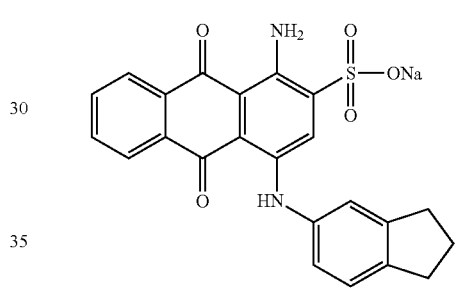

R$_f$: 0.4 (20% methanol in ethyl acetate).
$^1$H NMR (400 MHz, DMSO-d$_6$): δ 12.10 (s, 1H), 10.15 (brs, 1H), 8.30-8.26 (m, 2H), 7.96 (s, 1H), 7.88-7.81 (m, 2H), 7.50 (brs, 1H), 7.29 (d, J=8.0 Hz, 1H), 7.15 (s, 1H), 7.04 (dd, J=2.0, 8.0 Hz, 1H), 2.92-2.88 (m, 4H), 2.11-2.03 (m, 2H).
HRMS (ES): m/z for C$_{23}$H$_{17}$N$_2$O$_6$Na$_2$S [M+Na$^+$], calcd. 479.0654. found 479.0677.

SR-5-65: sodium 1-amino-9,10-dioxo-4-((5,6,7,8-tetrahydronaphthalen-1-yl)amino)-9,10-dihydroanthracene-2-sulfonate

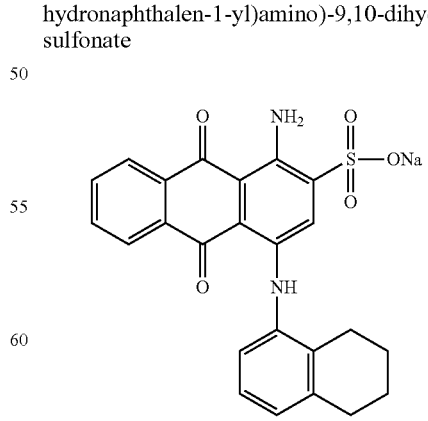

R$_f$: 0.4 (20% methanol in ethyl acetate).
$^1$H NMR (400 MHz, DMSO-d$_6$): δ 12.03 (s, 1H), 10.15 (brs, 1H), 8.31-8.28 (m, 2H), 7.88-7.83 (m, 2H), 7.83 (s, 1H), 7.50 (brs, 1H), 7.19 (t, J=7.6 Hz, 1H), 7.09 (d, J=7.6 Hz, 1H), 7.0 (d, J=7.2 Hz, 1H), 2.80 (t, J=5.6 Hz, 2H), 2.68 (t, J=5.6 Hz, 2H), 1.81-1.74 (m, 4H).

HRMS (ES): m/z for $C_{24}H_{16}N_2O_6Na_2S$ [M+Na$^+$], calcd. 493.0810. found 493.0797.

SR-5-68: sodium 1-amino-4-((3-benzylphenyl)amino)-9,10-dioxo-9,10-dihydroanthracene-2-sulfonate

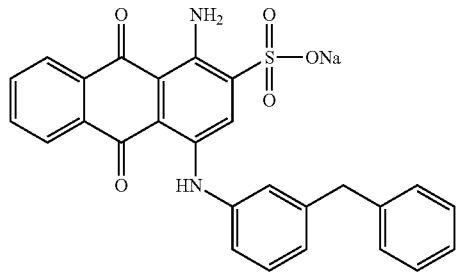

$R_f$: 0.4 (20% methanol in ethyl acetate).

$^1$H NMR (400 MHz, DMSO-d$_6$): δ 12.05 (s, 1H), 10.12 (brs, 1H), 8.30-8.26 (m, 2H), 8.07 (s, 1H), 7.87-7.84 (m, 2H), 7.51 (brs, 1H), 7.36 (t, J=7.6 Hz, 1H), 7.32 (s, 2H), 7.31 (s, 2H), 7.21-7.17 (m, 2H), 7.12 (d, J=8.0 Hz, 1H), 7.05 (d, J=7.6 Hz, 1H), 3.98 (s, 2H).

HRMS (ES): m/z for $C_{27}H_{16}N_2O_6Na_2S$ [M+Na$^+$], calcd. 529.0810. found 529.0834.

SR-5-69: sodium 1-amino-9,10-dioxo-4-((5,6,7,8-tetrahydronaphthalen-2-yl)amino)-9,10-dihydroanthracene-2-sulfonate

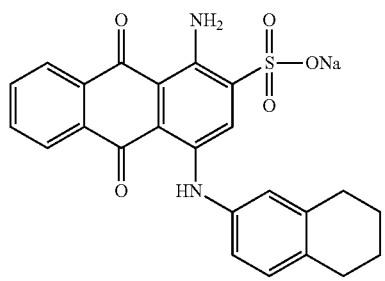

$R_f$: 0.4 (20% methanol in ethyl acetate).

$^1$H NMR (400 MHz, DMSO-d$_6$): δ 12.07 (s, 1H), 10.15 (brs, 1H), 8.30-8.27 (m, 2H), 7.97 (s, 1H), 7.88-7.82 (m, 2H), 7.49 (brs, 1H), 7.13 (d, J=8.0 Hz, 1H), 7.02-6.99 (m, 2H), 2.75 (brs, 4H), 1.77 (t, J=2.8 Hz, 4H).

HRMS (ES): m/z for $C_{24}H_{16}N_2O_6Na_2S$ [M+Na$^+$], calcd. 493.0810. found 493.0821.

SR-5-76: sodium 1-amino-4-((3-(tert-butyl)phenyl)amino)-9,10-dioxo-9,10-dihydroanthracene-2-sulfonate

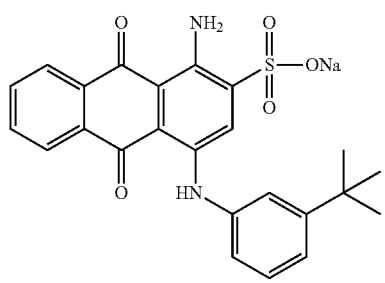

$R_f$: 0.4 (20% methanol in ethyl acetate).

$^1$H NMR (400 MHz, DMSO-d$_6$): δ 12.12 (s, 1H), 10.14 (brs, 1H), 8.30-8.27 (m, 2H), 8.11 (s, 1H), 7.88-7.83 (m, 2H), 7.52 (brs, 1H), 7.38 (t, J=8.0 Hz, 1H), 7.32 (t, J=1.6 Hz, 1H), 7.24 (d, J=7.6 Hz, 1H), 7.10 (dd, J=1.6, 7.6 Hz, 1H), 1.32 (s, 9H).

HRMS (ES): m/z for $C_{24}H_{21}N_2O_5Na_2S$ [M+Na$^+$], calcd. 495.0967. found 495.0944.

SR-5-88: 1-amino-9,10-dioxo-4-((3-(trifluoromethyl)phenyl)amino)-9,10-dihydroanthracene-2-carboxylic acid

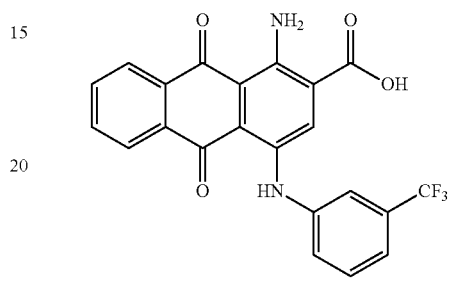

$R_f$: 0.5 (20% methanol in ethyl acetate).

$^1$H NMR (400 MHz, DMSO-d$_6$): 11.76 (s, 1H), 10.22 (brs, 2H), 8.33 (s, 1H), 8.28-8.22 (m, 2H), 7.88-7.81 (m, 2H), 7.64-7.59 (m, 3H), 7.44 (d, J=7.2 Hz, 1H).

HRMS (ES): m/z for $C_{22}H_{14}N_2O_4F_3$ [M+H$^+$], calcd. 427.0906. found 427.0917.

SR-5-91: sodium 4-((9H-fluoren-2-yl)amino)-1-amino-9,10-dioxo-9,10-dihydroanthracene-2-sulfonate

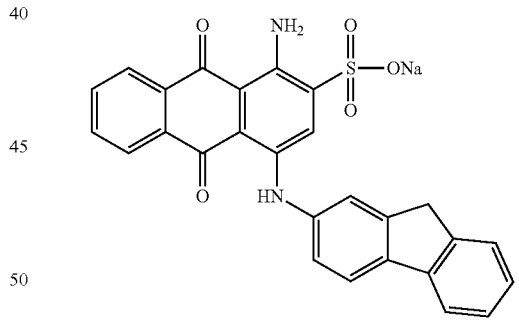

$R_f$: 0.4 (20% methanol in ethyl acetate).

$^1$H NMR (400 MHz, DMSO-d$_6$): δ 12.19 (s, 1H), 10.15 (brs, 1H), 8.32-8.29 (m, 2H), 8.08 (s, 1H), 7.97 (d, J=8.0 Hz, 1H), 7.90 (d, J=7.2 Hz, 1H), 7.88-7.86 (m, 2H), 7.60 (d, J=7.6 Hz, 1H), 7.52 (s, 1H), 7.40 (t, J=7.2 Hz, 1H), 7.34-7.29 (m, 2H), 3.97 (s, 2H).

HRMS (ES): m/z for $C_{27}H_{17}N_2O_6S$ [M−Na$^+$], calcd. 481.0858. found 481.0863.

SR-5-94: sodium 4-([1,1'-biphenyl]-3-ylamino)-1-amino-9,10-dioxo-9,10-dihydroanthracene-2-sulfonate

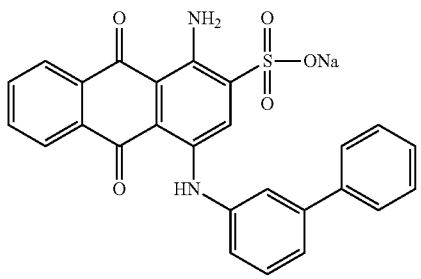

R$_f$: 0.4 (20% methanol in ethyl acetate).

$^1$H NMR (400 MHz, DMSO-d$_6$): δ 12.11 (s, 1H), 10.12 (brs, 1H), 8.31-8.28 (m, 2H), 8.18 (s, 1H), 7.90-7.84 (m, 2H), 7.75-7.73 (m, 2H), 7.58-7.47 (m, 5H), 7.42-7.38 (m, 1H), 7.29 (d, J=8.4 Hz, 1H).

HRMS (ES): m/z for C$_{26}$H$_{17}$N$_2$O$_6$Na$_2$S [M+Na$^+$], calcd. 515.0654. found 515.0648.

SR-5-72: sodium 1-amino-4-((naphthalen-2-yl)amino)-9,10-dioxo-9,10-dihydroanthracene-2-sulfonate

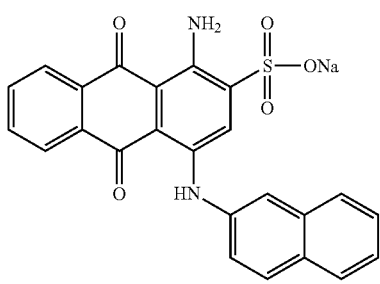

R$_f$: 0.4 (20% methanol in ethyl acetate).

$^1$H NMR (400 MHz, DMSO-d$_6$): δ 12.18 (s, 1H), 10.13 (brs, 1H), 8.32-8.29 (m, 2H), 8.11 (s, 1H), 8.01 (d, J=8.8 Hz, 1H), 7.94 (d, J=8.0 Hz, 1H), 7.91-7.85 (m, 3H), 7.78 (d, J=2.0 Hz, 1H), 7.55-7.46 (m, 3H).

SR-5-96: sodium 1-amino-4-((2-ethylphenyl)amino)-9,10-dioxo-9,10-dihydroanthracene-2-sulfonate

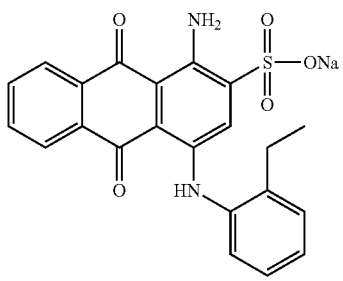

R$_f$: 0.4 (20% methanol in ethyl acetate).

$^1$H NMR (400 MHz, DMSO-d$_6$): δ 12.13 (s, 1H), 10.16 (brs, 1H), 8.31-8.29 (m, 2H), 7.88-7.82 (m, 2H), 7.78 (s, 1H), 7.41 (d, J=7.6 Hz, 1H), 7.34-7.23 (m, 3H), 2.67 (ABq, J=7.2 Hz, 2H), 1.22 (t, J=7.2 Hz, 3H).

HRMS (ES): m/z for C$_{22}$H$_{17}$N$_2$O$_6$Na$_2$S [M+Na$^+$], calcd. 467.0654. found 467.0613.

SR-5-97: sodium 1-amino-4-((4-ethylphenyl)amino)-9,10-dioxo-9,10-dihydroanthracene-2-sulfonate

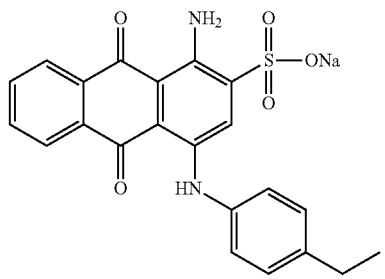

R$_f$: 0.4 (20% methanol in ethyl acetate).

$^1$H NMR (400 MHz, DMSO-d$_6$): δ 12.09 (s, 1H), 10.17 (brs, 1H), 8.30-8.26 (m, 2H), 8.00 (s, 1H), 7.88-7.82 (m, 2H), 7.49 (brs, 1H), 7.30 (d, J=8.4 Hz, 2H), 7.21 (d, J=8.8 Hz, 2H), 2.65 (ABq, J=8.0 Hz, 2H), 1.23 (t, J=8.0 Hz, 3H).

HRMS (ES): m/z for C$_{22}$H$_{17}$N$_2$O$_6$Na$_2$S [M+Na$^+$], calcd. 467.0654. found 467.0662.

SR-5-98: sodium 1-amino-4((2-isopropylphenyl)amino)-9,10-dioxo-9,10-dihydroanthracene-2-sulfonate

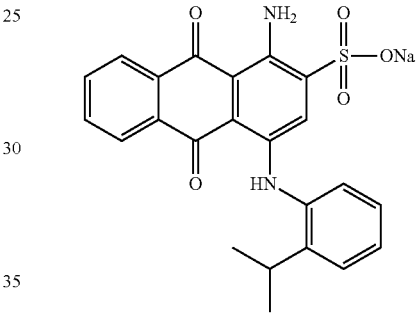

R$_f$: 0.4 (20% methanol in ethyl acetate).

$^1$H NMR (400 MHz, DMSO-d$_6$): δ 12.16 (s, 1H), 10.13 (brs, 1H), 8.31-8.29 (m, 2H), 7.89-7.83 (m, 2H), 7.73 (s, 1H), 7.49-7.46 (m, 1H), 7.32-7.24 (m, 3H), 3.23-3.16 (m, 1H), 1.25 (d, J=7.2 Hz, 6H).

HRMS (ES): m/z for C$_{23}$H$_{16}$N$_2$O$_6$Na$_2$S [M+Na$^+$], calcd. 481.0810. found 481.0798.

SR-5-99: sodium 1-amino-4-((4-isopropylphenyl)amino)-9,10-dioxo-9,10-dihydroanthracene-2-sulfonate

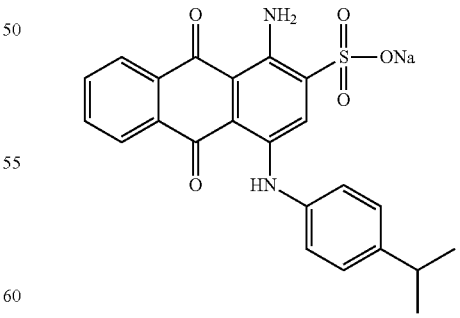

R$_f$: 0.4 (20% methanol in ethyl acetate).

$^1$H NMR (400 MHz, DMSO-d$_6$): δ 12.11 (s, 1H), 10.15 (brs, 1H), 8.30-8.27 (m, 2H), 8.02 (s, 1H), 7.88-7.83 (m, 2H), 7.51 (brs, 1H), 7.34 (d, J=8.4 Hz, 2H), 7.22 (d, J=8.8 Hz, 2H), 2.97-2.91 (m, 1H), 1.25 (d, J=6.4 Hz, 6H).

HRMS (ES): m/z for $C_{23}H_{16}N_2O_6Na_2S$ [M+Na$^+$], calcd. 481.0810. found 481.0827.

SR-5-66: sodium 1-amino-4-((naphthalen-1-ylamino)-9,10-dioxo-9,10-dihydroanthracene-2-sulfonate

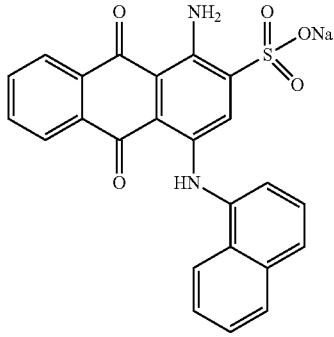

$R_f$: 0.4 (20% methanol in ethyl acetate).

$^1$H NMR (400 MHz, DMSO-d$_6$): δ 12.54 (s, 1H), 10.17 (brs, 1H), 8.35-8.31 (m, 2H), 8.10-8.04 (m, 2H), 7.91-7.86 (m, 3H), 7.82 (s, 1H), 7.65-7.60 (m, 3H), 7.52 (d, J=6.8 Hz, 1H).

The invention claimed is:

1. A method for treating urinary incontinence, the method comprising administering to the subject in need thereof a therapeutically effective amount of a compound having the general formula (I):

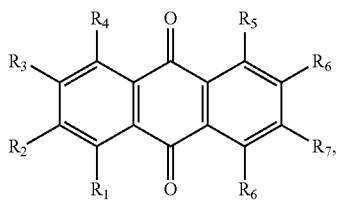

wherein in (I);
(i) $R_1$-$R_4$ and $R_7$ are each a hydrogen atom;
(ii) $R_5$ is an amine;
(iii) $R_8$ is a secondary amine, and
(iv) $R_6$ is a carboxyl group; or a pharmaceutically acceptable salt, hydrate, or isomer thereof.

2. The method of claim 1, wherein the compound has the general formula (IE):

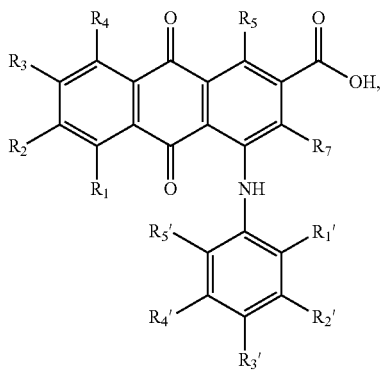

wherein in (IE);
(i) $R_{1'}$ and $R_{5'}$ are each independently selected from the group consisting of:
(a) a hydrogen atom;
(b) a substituent selected from the group consisting of a halide and an oxygen atom;
(c) a short chain alkyl, alkenyl, or alkynyl group, which can be branched or unbranched, substituted or unsubstituted, linear or cyclic;
(d) a short chain alkoxyl, alkenoxyl, or alkynoxyl group, which can be branched or unbranched, substituted or unsubstituted, linear or cyclic; and
(e) a short chain halo-alkyl, halo-alkenyl, or halo-alkynyl group, which can be branched or unbranched, substituted or unsubstituted, linear or cyclic;
(ii) $R_{2'}$ and $R_{4'}$ are each independently selected from the group consisting of:
(a) a hydrogen atom;
(b) a substituent selected from the group consisting of a halide, an oxygen atom, and an amine
(c) a short chain halo-alkyl, halo-alkenyl, or halo-alkynyl group, which can be branched or unbranched, substituted or unsubstituted, linear or cyclic;
(d) a sulfonate or carboxyl group;
(e) a short chain alkyl, alkenyl, or alkynyl group, which can be branched or unbranched, substituted or unsubstituted, linear or cyclic;
(f) a short chain alkoxyl, alkenoxyl, or alkynoxyl group, which can be branched or unbranched, substituted or unsubstituted, linear or cyclic;
(g) a nitrile group;
(h) a tetrazole; and
(i) a hydroxyl group; and
(iii) $R_{3'}$ is selected from the group consisting of:
(a) a hydrogen atom;
(b) a short chain halo-alkyl, halo-alkenyl, or halo-alkynyl group, which can be branched or unbranched, substituted or unsubstituted, linear or cyclic;
(c) a substituent selected from the group consisting of a halide, an oxygen atom, and an amine;
(d) a short chain alkyl, alkenyl, or alkynyl group, which can be branched or unbranched, substituted or unsubstituted, linear or cyclic
(e) a short chain alkoxyl, alkenoxyl, or alkynoxyl group, which can be branched or unbranched, substituted or unsubstituted, linear or cyclic; and
(f) a nitrile;
or a pharmaceutically acceptable salt, hydrate, or isomer thereof.

3. The method of claim 2, wherein $R_{1'}$ and $R_{5'}$ are each independently selected from the group consisting of:
a hydrogen atom;
(ii) fluoride;
(iii) a polycyclic group selected from the group consisting of a cycloalkane, cycloalkene, and cycloalkyne;
(iv) a methoxyl group; and
(v) a trifluoromethyl group.

4. The method of claim 2, wherein $R_{2'}$ and $R_{4'}$ are each independently selected from the group consisting of:
(i) a hydrogen atom;
(ii) fluoride;
(iii) chloride;
(iv) a trifluoromethyl group;
(v) a trifluoromethoxy group (—O—CF$_3$);
(vi) a methyl group;
(vii) an ethyl group;

(viii) an isopropyl group;
(ix) a tert-butyl group;
(x) a cyclopropyl group;
(xi) a nitrile group;
(xii) a methoxyl group;
(xiii) a ethoxyl group;
(xiv) an isopropoxyl group;
(xv) an amine, optionally a primary amine;
(xvi) a polycyclic group selected from the group consisting of cycloalkane, cycloalkene, and cycloalkyne;
(xvii) a benzyl group;
(xviii) a tetrazole; and
(xix) a hydroxyl group.

5. The method of claim 2, wherein $R_{3'}$ is selected from the group consisting of:
(i) a hydrogen atom;
(ii) a trifluoromethyl group;
(iii) fluoride;
(iv) chloride;
(v) a benzyl group;
(vi) a methyl group;
(vii) a methoxyl group;
(viii) an amine; and
(ix) a nitrile.

6. The method of claim 2, wherein $R_{2'}$ is a trifluoromethyl group, and each of $R_{1'}$, and $R_{3'}$-$R_{5'}$ is a hydrogen atom.

7. A method for treating urinary incontinence in a subject, the method comprising administering to the subject in need thereof a therapeutically effective amount of 1-amino-9,10-dioxo-4-(3-(trifluoromethyl)phenylamino)-9,10-dihydroanthracene-2-carboxylic acid, or a pharmaceutically acceptable salt or hydrate thereof.

* * * * *